US009447458B2

(12) United States Patent
Xu et al.

(10) Patent No.: US 9,447,458 B2
(45) Date of Patent: Sep. 20, 2016

(54) DETECTION OF NEIGHBORING VARIANTS

(75) Inventors: Ling Xu, Rockville, MD (US); Renee Howell, Rockville, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 817 days.

(21) Appl. No.: 13/297,970

(22) Filed: Nov. 16, 2011

(65) Prior Publication Data

US 2013/0122493 A1 May 16, 2013

(51) Int. Cl.
*C12Q 1/68* (2006.01)
*C07H 21/02* (2006.01)

(52) U.S. Cl.
CPC .......... *C12Q 1/6827* (2013.01); *C12Q 1/6883* (2013.01); *C12Q 2600/156* (2013.01)

(58) Field of Classification Search
CPC .......... C12Q 1/6827; C12Q 2525/204; C12Q 2527/107; C12Q 2531/107; C12Q 1/6883; C12Q 2600/156
See application file for complete search history.

(56) References Cited

U.S. PATENT DOCUMENTS

| 5,462,854 | A | 10/1995 | Coassin et al. |
|---|---|---|---|
| 5,554,501 | A | 9/1996 | Coassin et al. |
| 5,583,211 | A | 12/1996 | Coassin et al. |
| 5,688,643 | A | 11/1997 | Oka et al. |
| 5,776,677 | A | 7/1998 | Tsui et al. |
| 5,800,994 | A | 9/1998 | Martinelli et al. |
| 5,804,383 | A | 9/1998 | Gruenert et al. |
| 5,824,471 | A | 10/1998 | Mashal et al. |
| 5,856,092 | A | 1/1999 | Dale et al. |
| 5,981,178 | A | 11/1999 | Tsui et al. |
| 6,001,588 | A | 12/1999 | Tsui et al. |
| 6,174,670 | B1 | 1/2001 | Wittwer et al. |
| 6,197,498 | B1 | 3/2001 | Köster |
| 6,221,601 | B1 | 4/2001 | Köster et al. |
| 6,221,605 | B1 | 4/2001 | Köster |
| 6,235,478 | B1 | 5/2001 | Köster |
| 6,235,480 | B1 | 5/2001 | Shultz et al. |

(Continued)

FOREIGN PATENT DOCUMENTS

WO 2006/075172 A2 7/2006

OTHER PUBLICATIONS

Margraf, R.L. et al., J. Mol. Diagn., vol. 9, pp. 184-196 (2007).*

(Continued)

*Primary Examiner* — Teresa E Strzelecka
(74) *Attorney, Agent, or Firm* — Rothwell, Figg, Ernst & Manbeck, P.C.

(57) ABSTRACT

The present invention relates to methods, kits, probes, and systems for distinguishing between nucleotide variants that are close in proximity on a gene. The methods, kits, probes, and systems can include the use of a small amplicon assay in combination with two unlabeled probes in a high resolution thermal melting analysis of a biological sample containing a locus of interest in order to discern between disease-causing and benign variants that are close in proximity on a gene within the biological sample. The present invention also relates to method of detecting a disease in a patient based on the patient's genotype by determining whether the patient has a disease-causing variant at a locus of interest. The signature melt curves produced by the unlabeled probe tests can be analyzed using HRMA software to distinguish between disease-causing and benign variants that are close in proximity on a gene within the biological sample.

57 Claims, 6 Drawing Sheets

(56) References Cited

U.S. PATENT DOCUMENTS

| | | |
|---|---|---|
| 6,287,770 B1 | 9/2001 | Weston et al. |
| 6,300,076 B1 | 10/2001 | Köster |
| 6,447,661 B1 | 9/2002 | Chow et al. |
| 6,500,621 B2 | 12/2002 | Köster |
| 6,524,830 B2 | 2/2003 | Kopf-Sill |
| 6,589,485 B2 | 7/2003 | Köster |
| 6,602,662 B1 | 8/2003 | Köster et al. |
| 6,730,479 B2 | 5/2004 | Shultz et al. |
| 6,730,777 B1 | 5/2004 | Tsui et al. |
| 6,902,907 B1 | 6/2005 | Tsui et al. |
| 7,074,563 B2 | 7/2006 | Köster |
| 7,101,467 B2 | 9/2006 | Spaid |
| 7,217,571 B1 | 5/2007 | Gruenert et al. |
| 7,303,727 B1 | 12/2007 | Dubrow et al. |
| 7,390,457 B2 | 6/2008 | Schembri |
| 7,402,279 B2 | 7/2008 | Schembri |
| 7,419,787 B2 | 9/2008 | Köster |
| 7,452,565 B2 | 11/2008 | Banerjee et al. |
| 7,456,281 B2 | 11/2008 | Dujols |
| 7,544,793 B2 | 6/2009 | Gao et al. |
| 7,563,569 B2 | 7/2009 | Seul et al. |
| 7,604,938 B2 | 10/2009 | Takahashi et al. |
| 7,629,124 B2 | 12/2009 | Hasson et al. |
| 7,759,065 B2 | 7/2010 | Köster |
| 2002/0142300 A1* | 10/2002 | Bernard ............... C12Q 1/6827 435/6.16 |
| 2002/0197630 A1 | 12/2002 | Knapp et al. |
| 2003/0064370 A1 | 4/2003 | Weston et al. |
| 2005/0042639 A1 | 2/2005 | Knapp et al. |
| 2005/0233335 A1 | 10/2005 | Wittwer et al. |
| 2006/0019253 A1 | 1/2006 | Wittwer et al. |
| 2006/0147938 A1 | 7/2006 | Accola et al. |
| 2007/0020672 A1 | 1/2007 | Wittwer et al. |
| 2007/0026421 A1 | 2/2007 | Sundberg et al. |
| 2007/0231799 A1 | 10/2007 | Knight et al. |
| 2008/0003593 A1 | 1/2008 | Hasson et al. |
| 2008/0138803 A1 | 6/2008 | Galvan-Goldman et al. |
| 2008/0287379 A1 | 11/2008 | Tabatadze et al. |
| 2009/0112481 A1 | 4/2009 | Cao |
| 2009/0112484 A1 | 4/2009 | Boles et al. |
| 2009/0117553 A1 | 5/2009 | Wittwer et al. |
| 2009/0215105 A1 | 8/2009 | Hammer et al. |
| 2009/0222503 A1 | 9/2009 | Palais et al. |
| 2009/0248349 A1 | 10/2009 | Hasson et al. |
| 2009/0263820 A1 | 10/2009 | Seul et al. |
| 2009/0318306 A1 | 12/2009 | Hasson et al. |
| 2009/0324037 A1 | 12/2009 | Hasson et al. |
| 2010/0047875 A1 | 2/2010 | Gao et al. |
| 2010/0191482 A1 | 7/2010 | Hasson et al. |
| 2010/0233687 A1 | 9/2010 | Cao |
| 2011/0056926 A1 | 3/2011 | Coursey |

OTHER PUBLICATIONS

GenBank Accession No. AJ574977 (Nov. 2006).*
Chou, et al., "Characterization of the Promoter Region of the Cystic Fibrosis Transmembrane Conductane Regulator Gene," J. Biol. Chem., vol. 266, No. 36, pp. 24471-24476 (1991).
Dames, et al., "Unlabeled Probes for the Detection and Typing of Herpes Simplex Virus," Clin. Chem., 53:10, pp. 1847-1854 (2007).
Desgeorges, et al., "A Healthy Male with Compound and Double Heterozygosities for ΔF508, F508C, and M47OV in Exon 10 of the Cystic Fibrosis Gene," Am. J. Hum. Genet., 54: 384-385 (1994).
Erali, et al., "High Resolution Melting Applications for Clinical Laboratory Medicine," Experimental Molecular Pathology, 85(1), 19 pages (2008).
Herrmann, et al., "Amplicon DNA Melting Analysis for Mutation Scanning and Genotyping: Cross-Platform Comparison of Instruments and Dyes," Clinical Chemistry 52(3):494-503 (2006).
Innis, et al., "DNA sequencing with Thermus aquaticus DNA polymerase and direct sequencing of polymerase chain reaction-amplified DNA," Proc. Natl. Acad. Sci. USA, vol. 85, pp. 9436-9440 (Dec. 1988).
Johnson, et al., "A Comparative Study of Five Technologically Diverse CFTR Testing Platforms," Journal of Molecular Diagnostics, vol. 9, No. 3, pp. 401-407 (Jul. 2007).
Kerem, et al., "Identification of the cystic fibrosis gene: genetic analysis," Science, vol. 245, No. 4922, pp. 1073-1080 (Sep. 8, 1989) (abstract) 1 page.
Kerem, et al., "A Missense Cystic Fibrosis Transmembrane Conductance Regulator Mutation With Variable Phenotype," Pediatrics, vol. 100, No. 3, pp. 1-6 (Sep. 1997).
Kobayashi, et al., "Benign Missense Variations in the Cystic Fibrosis Gene," Am. J. Hum. Genet., 47:611-615 (1990).
Lee, et al., "In vitro cytotoxicity of GC sequence directed alkylating agents related to distamycin," J. Med. Chem., 36 (7): 863-870 (Apr. 2, 1993) (abstract) 1 page.
Liew, et al., "Genotyping of Single-Nucleotide Polymorphisms by High-Resolution Melting of Small Amplicons," Clinical Chemistry, 50:7, pp. 1156-1164 (2004).
Litia, et al., "Detection of Mutation ΔF508 in the Cystic Fibrosis Gene Using Allele-specific PCR Primers and Time-resolved Fluorometry," Genome Res., 2:157-162 (1992).
Pallares-Ruiz, et al., "Complete mutational screening of the cystic fibrosis transmembrane conductance regulator gene: cystic fibrosis mutations are not involved in healthy men with reduced sperm quality," Human Reproduction, vol. 14, No. 12, pp. 3035-3040 (1999).
Pierce, et al., "LATE-PCR and allied technologies: real-time detection strategies for rapid, reliable diagnosis from single cells," Methods Mol. Biol., 688:47-66 (2011) (abstract) 1 page.
Poulson, et al., "Closed-tube genotyping of apolipoprotein E by isolated-probe PCR with multiple unlabeled probes and high-resolution DNA melting analysis," BioTechniques, vol. 43, No. 1, pp. 87-91 (Jul. 2007).
Ririe, et al., "Product differentiation by analysis of DNA melting curves during the polymerase chain reaction," Analytical Biochemistry 245(2):154-160 (Feb. 15, 1997) (abstract) 1 page.
Rowntree, et al., "The Phenotypic Consequences of CFTR Mutations," Annals of Human Genetics, 67:471-485 (2003).
Vossen, et al., "High-throughput Genotyping of Mannose-binding Lectin Variants Using High-resolution DNA-melting Analysis," Human Mutation, Mutation in Brief 31: E1286-E-1293 (2010) (Online).
Wittwer, et al., "High-Resolution Genotyping by Amplicon Melting Analysis Using LCGreen," Clinical Chemistry, 49:6, pp. 853-860 (2003).
Zhou, et al., "Snapback Primer Genotyping with Saturating DNA Dye and Melting Analysis," Clin. Chem., 54:10. pp. 1648-1656 (2008).
Zhou, et al., "High-Resolution DNA Melting Analysis for Simultaneous Mutation Scanning and Genotypng in Solution," Clinical Chemistry, 51:10, pp. 1770-1777 (2005).
Mason et al., "Detection of multiple cystic fibrosis transmembrane conductance regulator (CFTR) mutations using high resolution thermal melt analysis on a microfluidic chip," 40th Annual Oak Ridge Conference Breakthrough Technologies for Clinical Diagnostics, Poster 70, Apr. 17 & 18, 2008.
Montgomery et al., "Simultaneous mutation scanning and genotyping by high-resolution DNA melting analysis," Nature Protocols, vol. 2, No. 1, pp. 59-66, Feb. 22, 2007.

* cited by examiner

DETECTION OF NEIGHBORING VARIANTS

SEQUENCE SUBMISSION

The present application contains a Sequence Listing which has been submitted in electronic format. The Sequence Listing is entitled 3400237SequenceListing.txt, created on Jan. 11, 2012 and is 9 kb in size. The information in the electronic format of the Sequence Listing is part of the present application and is incorporated herein by reference in its entirety.

BACKGROUND

1. Field of the Invention

The present invention relates to methods, kits, primers, probes, and systems for distinguishing between nucleotide variants that are close in proximity on a gene. More particularly, aspects of the present invention relate to methods, kits, primers, probes, and systems for using a small amplicon assay in combination with unlabeled probes in conducting a high resolution thermal melting analysis of a biological sample containing a locus of interest in order to discern between disease-causing and benign variants that are close in proximity on a gene. The present invention also relates to methods of detecting a disease in a patient based on the patient's genotype by determining whether the patient has a disease-causing variant at a locus of interest on the patient's genome.

2. Description of the Background

Melt curve analysis or high resolution thermal melting is an important technique for analyzing nucleic acids. In accordance with some methods, a double stranded nucleic acid is denatured in the presence of a dye that indicates whether the two strands are bound or not. Examples of such indicator dyes include non-specific binding dyes such as SYBR® Green I, whose fluorescence efficiency depends strongly on whether it is bound to double stranded DNA. As the temperature of the mixture is increased, a reduction in fluorescence from the dye indicates that the nucleic acid molecule has melted, i.e., unzipped, partially or completely. Thus, by measuring the dye fluorescence as a function of temperature, information is gained regarding the length of the duplex, the GC content or even the exact sequence. See, e.g., Ririe et al. (Anal Biochem 245:154-160, 1997), Wittwer et al. (Clin Chem 49:853-860, 2003), Liew et al. (Clin Chem 50:1156-1164 (2004), Herrmann et al. (Clin Chem 52:494-503, 2006), Knapp et al. (U.S. Patent Application Publication No. 2002/0197630), Wittwer et al. (U.S. Patent Application Publication No. 2005/0233335), Wittwer et al. (U.S. Patent Application Publication No. 2006/0019253), Sundberg et al. (U.S. Patent Application Publication No. 2007/0026421) and Knight et al. (U.S. Patent Application Publication No. 2007/0231799).

A number of commercial instruments exist that perform thermal melts on DNA. Examples of available instruments include the Idaho Technology HR-1 high resolution melter and the Idaho Technology LightScanner high resolution melter. The HR-1 high resolution melter has a high resolution fluorescent signal to noise ratio and temperature resolution. However, it suffers from a limitation that it can only analyze one sample at a time, and the sample container must be replaced manually. Replacement of the container for each test may contribute to run-to-run temperature variability. The LightScanner high resolution melter also has good signal and temperature resolution, and operates on a 96-well plate sample container. A typical mode of operation for these analyzers is to apply heat to the sample(s) in a controlled manner to achieve a linear rise in temperature versus time. Simultaneously, a stable continuous fluorescence excitation light is applied, and emitted fluorescence is collected continuously over fixed integration time intervals. The fluorescence intensity data is converted from a time basis to a temperature basis based on the knowledge of the temperature ramp versus time.

In addition to such commercial instruments, microfluidic systems have also been developed for performing thermal melt analysis. For example, Sundberg et al. (U.S. Patent Application Publication No. 2007/0026421) and Knight et al. (U.S. Patent Application Publication No. 2007/0231799), each incorporated by reference herein, describe methods, systems, kits and devices for conducting binding assays using molecular melt curves in microfluidic devices. Molecule(s) to be assayed can be flowed through microchannels in the devices where the molecule(s) optionally are exposed to additional molecules constituting, e.g., fluorescence indicator molecules and/or binding partners of the molecule being assayed. The molecules involved are then heated (and/or cooled) and a detectable property of the molecules is measured over a range of temperatures. From the resulting data, a thermal property curve(s) is constructed which allows determination and quantification of the binding affinity of the molecules involved. Other microfluidic systems useful for thermal melting analysis are described in Hasson et al. (U.S. Patent Application Publication No. 2009/0248349), Hasson et al. (U.S. Patent Application Publication No. 2009/0318306), Hasson et al. (U.S. Patent Application Publication No. 2009/0324037), Cao (U.S. Patent Application Publication No. 2010/0233687) and Coursey (U.S. Patent Application Publication No. 2011/0056926).

Although high resolution thermal melting is a useful tool for genotyping, many genotyping assay attempts do not present a significant difference in the melt curves of targeted variants, especially variants that are in close proximity. For example, prior techniques for Cystic Fibrosis (CF) testing using high resolution thermal melt analysis lacked the ability to discern between benign and disease-causing variants in close proximity in Exon 10 of the CFTR (cystic fibrosis transmembrane conductance regulator) gene.

Cystic fibrosis, also known as mucoviscidosis, is the most common lethal autosomal recessive disorder and the most common life-shortening inherited diseases among the Caucasian population. Cystic Fibrosis is caused by mutations of the CFTR gene. This disease affects multiple systems and organs in the body, including the lungs, pancreas, intestines, and liver, and occurs in 1 in 2,500 Caucasian newborns (Rowntree and Harris, Annals of Human Genetics. 2003; 67:471-485). Currently, more than 30,000 children and young adults are affected by Cystic Fibrosis in the United States. The ΔF508 mutation, a three base pair deletion that removes a phenylalanine residue at amino acid position 508 (ΔF508), is the mutation occurring on the majority of CF chromosomes being found on 70%-75% of North American CF chromosomes (Kerem et al., Science. 1989; 245:1073-1080). This three base pair deletion affects the cytoplasmic nucleotide-binding domain (NBD-1) and causes severe dysfunction of chloride transportation a cross cellular membranes.

Since ΔF508 was first identified in CF gene by Kerem and his colleagues using restriction fragment length polymorphisms (RFLP), more techniques have been used to explore CF mutations, such as a restriction map of the genomic clone (Chou et al., J. Biol. Chem. 1991; 266:24471-24476), denaturing gel gradient electrophoresis (DGGE) using PCR (Pallares-Ruiz et al. Human Reproduction. 1999; 14:3035-3040), allele-specific primers and fluorometry (Litia et al. Genome Res. 1992; 2:157-162), DNA sequencing (Kerem et al. Pediatrics. 1997; 100:1-6), and saturated dye and melting analysis (Zhou et al. Clin. Chem. 2008; 54:1648-1656). These techniques enhanced the understanding of the structures of the CFTR gene and CFTR mutations related to the CF disease, providing a promising outlook for early diagnosis and treatments to the CF patients.

However, it has been discovered that the benign variants F508C, I507V, and I506V that neighbor ΔF508/ΔI507, often present similar genotype patterns and are mistakenly recognized as the disease-causing variants ΔF508 or ΔI507 (Desgeorges et al. Am J Hum Genet. 1994; 54:384-5). The substitution of cysteine for phenylalanine 508 (F508C) and substitution of valine for isoleucine 506 (I506V) have been reported to be homologous for ΔF508 mutation and are difficult to be distinguished from ΔF508 (Kobayashi et al. Am. J. Hum. Genet. 1990; 47:611-615). ΔI507, a three base pair in frame deletion close to ΔF508 that results in the deletion of isoleucine, has been reported to present the same genotyping pattern as I506V, a benign variant at the same location of ΔI507 (Johnson et al., J Mol Des 2007; 9:401-407).

Although commercial kits are available to detect CF mutations, these kits do not make it possible to distinguish between all benign and disease-causing mutations in Exon 10 in a rapid detection system (Johnson et. al., J. Mol. Diagn. 2007. 9:401-407). It is critical and necessary for researchers, physicians, and diagnostic laboratories to be able to differentiate ΔF508 and ΔI507 from F508C, I507V, and I506V in order to reliably detect and diagnose disease-causing genotypes.

Accordingly, there is a need in the art for reliable methods, kits, probes, and systems that will be useful in discerning between nucleotide sequence variants that present similar genotype patterns. Similarly, there is a need for methods, kits, probes, and systems for accurately detecting a disease in a patient when a disease-causing variant may be mistakenly recognized as a benign variant because the variants present similar melting signatures.

SUMMARY

In one aspect, the present invention provides a method of distinguishing between at least two variants on a target nucleic acid having a locus of interest. In one embodiment, the method comprises (a) providing a first aliquot of a nucleic acid having a locus of interest; (b) incubating the first aliquot of the nucleic acid with a limiting primer, an excess primer, and a first probe that is designed to hybridize to the locus of interest on a target strand of the nucleic acid; (c) performing asymmetric PCR using the first aliquot to produce an excess of amplicons corresponding to the target strand to which the first probe hybridizes, thereby producing a first probe element; (d) providing a second aliquot of the nucleic acid having a locus of interest; (e) incubating the second aliquot of the nucleic acid with the limiting primer, the excess primer, and a second probe that is designed to hybridize to the locus of interest on the target strand, wherein the first probe differs in sequence from the second probe; (f) performing asymmetric PCR using the second aliquot to produce an excess of amplicons corresponding to the target strand to which the second unlabeled probe hybridizes, thereby producing a second probe element; (g) generating a first melting curve for the first probe element in a first mixture with a saturating binding dye by measuring fluorescence from the dye as the first mixture is heated; (h) generating a second melting curve for the second probe element in a second mixture with the saturating binding dye by measuring fluorescence from the dye as the second mixture is heated; and (i) analyzing the first melting curve and the second melting curve to distinguish between the at least two nearby neighbor variants, wherein a melting signature curve of each of the at least two nearby neighbor variants is different in the first and second melting curves.

In one embodiment, one or both of the first and second probes can be unlabeled.

In one embodiment, the locus of interest is on a gene associated with a disease or disorder such as Cystic Fibrosis, Factor V Leiden, a RET proto-oncogene associated disease, lactase hemorrhagic telangiectasia, and hereditary hemorrhagic telangiectasia. Alternatively, the present invention can be used to identify or determine polymorphisms, such as human platelet antigens.

In another embodiment, the method steps can include (a) providing an amplicon having a locus of interest; (b) hybridizing a first unlabeled probe to the locus of interest on a first portion of the amplicon to form a first probe element; (c) hybridizing a second unlabeled probe to the locus of interest on a second portion of the amplicon to form a second probe element, (d) generating a first melting curve for the first probe element; (e) generating a second melting curve for the second probe element; and (f) analyzing the first melting curve and the second melting curve to distinguish between the at least two nearby neighbor variants. In one embodiment, the melting curves are generated in the presence of an intercalating or saturation dye by measuring the fluorescence as the probe element is heated.

In another aspect, the present invention provides a method of distinguishing between at least two variants on a target nucleic acid having a locus of interest comprising (a) mixing a first portion of a target nucleic acid having a locus of interest with a first primer and a second primer, the primers configured for amplifying the target nucleic acid having a locus of interest, and a first unlabeled probe; (b) in parallel, mixing a second portion of said target nucleic acid having a locus of interest with the first primer, the second primer, and a second unlabeled probe; (c) simultaneously and asymmetrically amplifying the target nucleic acid having a locus of interest to generate amplicons that hybridize to the first unlabeled probe and the second unlabeled probe to form a first probe element and a second probe element, respectively; (d) generating a first melting curve for the first probe element; (e) sequentially or simultaneously generating a second melting curve for the second probe element; and (f) analyzing the first melting curve and the second melting curve to distinguish between the at least two nearby neighbor variants.

In another aspect, the present invention provides a method of detecting a disease in a patient based on the patient's genotype and a priori knowledge of benign and disease-causing variant gene sequences associated with the disease. In one embodiment, the method comprises the steps of (a) obtaining a biological sample from the patient; (b) subjecting a first portion of the biological sample to asymmetric PCR involving a limiting primer, an excess primer, and a first probe to produce a first probe-amplicon element; (c) subjecting a second portion of the biological sample to asymmetric PCR involving the limiting primer, the excess primer, and a second probe to produce a second probe-amplicon element; (d) generating a first melting curve and a second melting curve by subjecting the first and second probe-amplicon melting elements to high resolution thermal melting analysis, respectively; (e) distinguishing between a benign variant and a disease-causing neighbor variant by analyzing the first melting curve and the second melting curve, wherein a probe melting signature curve of the benign variant and a probe melting signature curve of the disease-causing variant in the first and second melting curves are different; and (f) determining whether the patient has a disease-causing variant.

In another aspect, the present invention provides a method of detecting a disease in a patient based on the patient's genotype and a priori knowledge of benign and disease-causing variant gene sequences associated with the disease. In one embodiment, the method comprises the steps of (a) obtaining a biological sample from a patient wherein the biological sample includes a nucleic acid that has a locus of interest; (b) incubating a first portion of the sample with a limiting primer, an excess primer, and a first unlabeled probe; (c) incubating a second portion of the sample with the limiting primer, the excess primer, and a second unlabeled probe; (d) subjecting each of the incubating first and second portions to asymmetric PCR in order to produce an excess of small amplicons having the locus of interest; (e) once the limiting primer is exhausted, subjecting the first portion of the small amplicon to a first unlabeled probe assay to produce a first melting curve and subjecting a second portion of the small amplicon having a locus of interest to a second unlabeled probe assay to produce a second melting curve; (f) distinguishing between a benign variant and a disease-causing neighbor variant by analyzing the first melting curve and the second melting curve, wherein a probe melting signature curve of the benign variant and a probe melting signature curve of the disease-causing variant in the first and second melting curves are different; and (g) determining whether the patient has a disease-causing variant.

In one embodiment, the disease to be detected can be a disease or disorder such as Cystic Fibrosis, Factor V Leiden, a RET proto-oncogene associated disease, lactase hemorrhagic telangiectasia, or hereditary hemorrhagic telangiectasia. Alternatively, the present invention can be used to identify or determine polymorphisms, such as human platelet antigens.

In another embodiment, the present invention provides a method of detecting a disease in a patient based on the patient's genotype and a priori knowledge of benign and disease-causing variant gene sequences associated with the disease. In one embodiment, the method comprises (a) obtaining a biological sample from a patient; (b) subjecting the sample to asymmetric PCR to produce a small amplicon having a locus of interest; (c) subjecting a first portion of the small amplicon to a first unlabeled probe assay to produce a first melting curve; (d) subjecting a second portion of the small amplicon having a locus of interest to a second unlabeled probe assay to produce a second melting curve; (e) distinguishing between a benign variant and a disease-causing neighbor variant by analyzing the first melting curve and the second melting curve, wherein a probe melting signature curve of the benign variant and a probe melting signature curve of the disease-causing variant in the first and second melting curves are different; and (f) determining whether the patient has a disease-causing variant.

In another embodiment, the method of detecting a disease in a patient based on the patient's genotype and a priori knowledge of benign and disease-causing variant gene sequences associated with the disease comprises (a) obtaining a biological sample from a patient; (b) dividing the biological sample into a first portion and a second portion; (c) performing asymmetric PCR in order to produce a small amplicon having a locus of interest in each of the first portion and the second portion; (c) subjecting the first portion to a first unlabeled probe assay to produce a first melting curve; (d) simultaneously or sequentially subjecting the second portion to a second unlabeled probe assay to produce a second melting curve; (e) distinguishing between a benign variant and a disease-causing neighbor variant by comparing the first melting curve and the second melting curve; and (f) determining whether the patient has a disease-causing variant.

In some embodiments, the present invention includes the use of a first probe and a second probe, wherein the first and second probes have sequences that differ from each other. In some embodiments, the first and second probes are unlabeled.

In another aspect, the present invention provides a method of distinguishing between at least two nearby neighbor variants on a nucleic acid having a locus of interest by (a) performing asymmetric PCR using a primer pair and a first unlabeled probe; (b) performing asymmetric PCR using the primer pair and a second unlabeled probe, wherein the first unlabeled probe differs in sequence from the second unlabeled probe; (c) generating a first melting curve for products produced in the asymmetric PCR using the first unlabeled probe in a first mixture with a saturating binding dye by measuring fluorescence from the dye as the first mixture is heated; (d) generating a second melting curve for products produced in the asymmetric PCR using the second unlabeled probe in a second mixture with the saturating binding dye by measuring fluorescence from said dye as the second mixture is heated; and (e) analyzing the first melting curve and the second melting curve to distinguish between the at least two nearby neighbor variants, wherein a melting signature curve of each of the at least two nearby neighbor variants is different in the first and second melting curves.

In one embodiment, each of the asymmetric PCRs in steps (a) and (b) produce PCR products comprising small double-stranded amplicons and probe/primer amplicons. In some embodiments, if two neighboring mutations cannot be clearly separated from melt signatures produced by the probe/primer amplicons, the method further includes the step of using melt signatures produced by the small double-stranded amplicons to distinguish between the at least two nearby neighbor variants. In certain embodiments, melting of the small double-stranded amplicons and the probe/primer amplicons will provide thermal melt data for each type of amplicon, which can be used to distinguish between the at least two nearby neighbor variants. Thus, the method may include the further step of analyzing melt data from both the small double-stranded amplicons and from the probe/primer amplicons to distinguish between the at least two nearby neighbor variants.

In another aspect, the present invention provides a kit for distinguishing between at least two variants on a target nucleic acid having a locus of interest and/or detecting a disease in a patient based on the patient's genotype. In one embodiment, the kit comprises a first unlabeled probe and a second unlabeled probe, wherein the first and second unlabeled probes have sequences that differ from each other. In another embodiment, the kit may further comprise primers for amplifying a locus of interest on a target nucleic acid. In one embodiment, the primers are selected for an asymmetric PCR amplification reaction. In a further embodiment, the kit may also comprise instructions for performing an amplification reaction and/or thermal analysis. The kit may also comprise a dye that distinguishes between double stranded and single stranded nucleic acids. A suitable dye may be an intercalating dye, a saturation dye or a double stranded DNA (dsDNA) binding dye.

In another aspect, the present invention provides a system for distinguishing between at least two variants on a target DNA and/or detecting a disease in a patient based on the patient's genotype. In one embodiment, a system for distinguishing between at least two nearby neighbor variants on a nucleic acid having a locus of interest according to the present invention can include (a) a microfluidic device having a plurality of sample loading zones, each of the sample loading zones being configured to house a separate asymmetric PCR using a nucleic acid having a locus of interest; (b) a HRMA device, comprising a heating element, a fluorescence excitation light source and a fluorescence collection aperture; and (c) a fluorescence derivative melting curve analysis device configured to compare at least two melting curves generated by the HRMA device so as to distinguish between at least two nearby neighbor variants on the nucleic acid having a locus of interest.

In one embodiment, the microfluidic device has at least two sample loading zones that are loaded with a limiting primer, an excess primer, and an unlabeled probe. In certain embodiments, at least one of the at least two sample loading zones that are loaded with an unlabeled probe contains a first unlabeled probe as the loaded unlabeled probe and at least one of the at least two sample loading zones that are loaded with an unlabeled probe contains a second unlabeled probe as the loaded unlabeled probe. In some embodiments, the HRMA device is configured to thermally melt probe-amplicon elements obtained from asymmetric PCRs in said sample loading zones, and to generate fluorescence derivative melting curves for said probe-amplicon elements.

In some embodiments, the amplicon having a locus of interest is produced by mixing a target nucleic acid having a locus of interest with a first primer and a second primer, where the primers are designed to amplify the target nucleic acid having a locus of interest, and amplifying the target nucleic acid having a locus of interest to generate an amplicon having the locus of interest. In some embodiments, the method steps are performed simultaneously. In other embodiments, the method steps are performed sequentially.

In some embodiments, unlabeled probes are designed to each have a sequence that is complementary to the wild-type sequence. In some embodiments, a first primer and a second primer are each set close to the targeted variants to reduce the amplicon size for high genotyping sensitivity. In some embodiments, unlabeled probes are designed so as to have one or more base pair mismatches at the locus of interest when the target nucleic acid has a variant sequence. For example, in some embodiments, the unlabeled probes are designed to have one base pair mismatch at the locus of interest. In other embodiments, the unlabeled probes may have a plurality of base pair mismatches, e.g., 3 bp mismatch in the case of a full codon deletion. In another embodiment, the unlabeled probes may have five or more base pair mismatches at the locus of interest. In some embodiments, an unlabeled probe has 2 to 5 nucleotides at its 5'-end prior to the locus of interest, preferably 2 or 3 nucleotides at its 5'-end prior to the targeted variants. In some embodiments, a second unlabeled probe has 5 nucleotides at its 5'-end prior to the targeted variants. In some embodiments, an unlabeled probe Tm is less than about 5° C. lower than primer Tms and the difference of a first primer's Tm and a second primer's Tm is less than about 1° C.

In some embodiments, a first unlabeled probe and a second unlabeled probe are each 34 to 37 nucleotides in length. In some embodiments, a first probe and a second probe are blocked at their 3' ends.

In some embodiments, an amplicon having a locus of interest is produced using asymmetric PCR. In some embodiments, a first primer is a limiting primer in the asymmetric PCR. In some embodiments, a second primer is an excess primer in the asymmetric PCR.

In some embodiments, the melting curves of the probe elements are generated in the presence of an indicator dye by measuring the fluorescence as the probe element is heated. As used herein, an indicator dye is a dye that distinguishes between double stranded and single stranded nucleic acids as described herein. In other embodiments, the melting curves of the probe assays are generated in the presence of an indicator dye by measuring the fluorescence as the assay mixture is heated.

It is within the scope of the invention to obtain high resolution thermal melting curves using at least two unlabeled probes for target DNA sequences. It is also within the scope of the invention to design probes and primers that are suitable for use in discerning between variants in close proximity on the nucleic acid of interest. In one embodiment, two or more unlabeled probes are designed to hybridize to the same locus of interest on the target nucleic acid, but to produce different melting signature curves so as to provide meaningful data to be used to distinguish between variants that present indistinguishable melting curves using typical genotyping protocols.

Thus, in another aspect, the present invention also provides a method of designing primers and probes that are useful for thermal melt analysis of a locus of interest that contains one or more benign variants and one or more disease-causing variants that are in close proximity on the locus of interest. In accordance with this aspect, the method comprises (a) selecting a locus of interest of a disease, in which the locus has benign variants and disease-causing variants in close proximity, (b) designing a pair of primers for use in asymmetric PCR, and (c) designing at least two probes for hybridizing to one strand of the locus of interest. In one embodiment, close proximity means within about 3-15 nucleotides, preferably within 3-10 and more preferably within 3-7 nucleotides of each other. In some embodiments the primers have a Tm difference of less than about 1° C. and are selected to produce an amplicon of about 60 base pairs or longer upon amplification of the locus of interest. In some embodiments, the PCR produces amplicons that are between 70 and 130 bp in length. In certain embodiments, the PCR produces amplicons that are between 80 and 100 bp in length. In some embodiments, the nucleotide sequence of each probe is complementary to the wild-type sequence of the locus of interest. In other embodiments each probe has a Tm that is less 5° C. lower than the Tms of the primers. In some embodiments, each probe overlaps the nucleotide positions of the one or more benign and one or more disease-causing variants that are in close proximity on the locus of interest. In one embodiment, the probes differ in length. In some embodiments, the probes differ in length as a result of the addition of residues at the 5' end of the probe. In some embodiments, the probes each have a 3' end block to prevent extension.

The above and other aspects and features of the present invention, as well as the structure and application of various embodiments of the present invention, are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of the reference number identifies the drawing in which the reference number first appears.

DETAILED DESCRIPTION OF PREFERRED EMBODIMENTS

Figure 1:
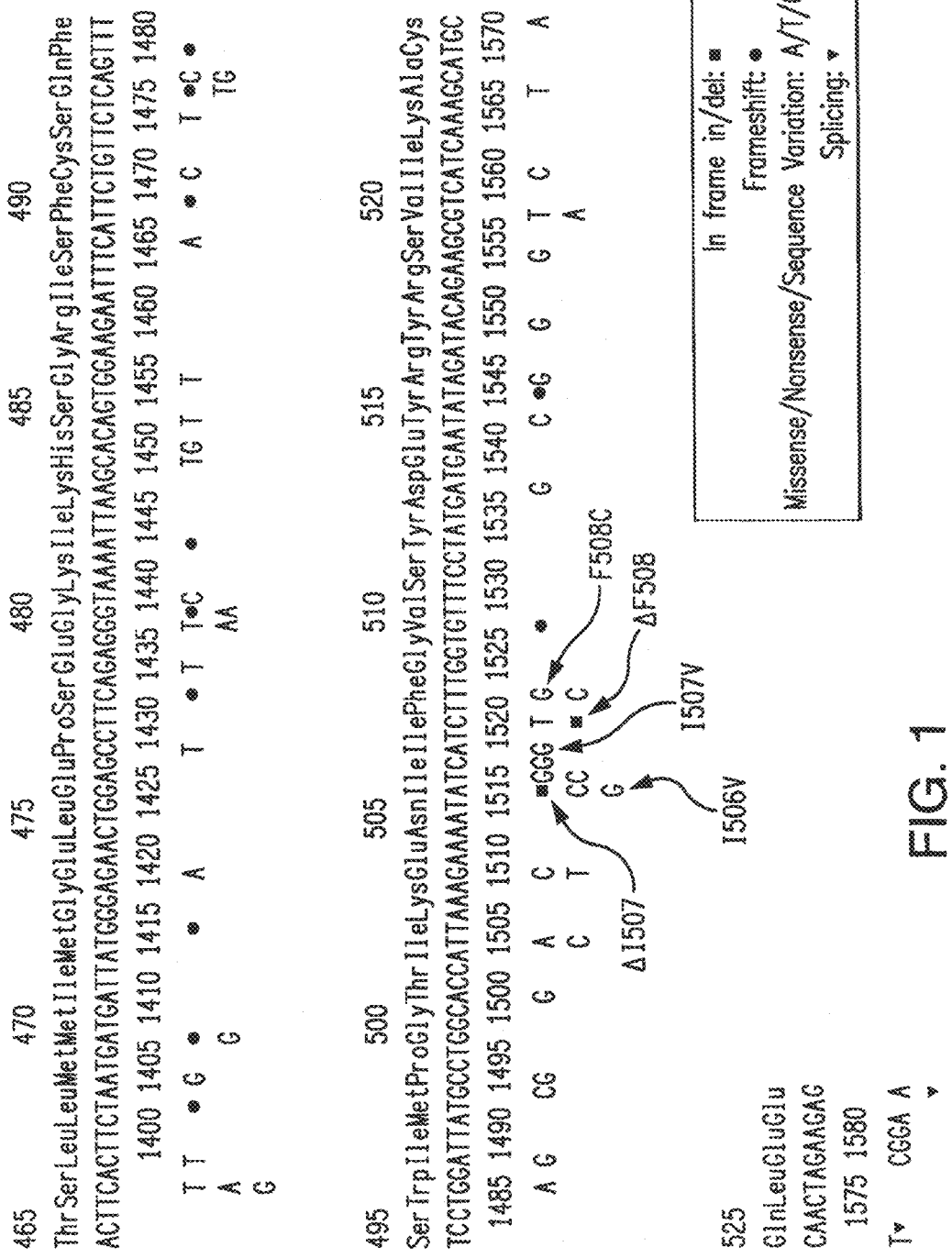
FIG. 1 is a gene map illustrating an embodiment of the invention showing the mutations of ΔF508, ΔI507, F508C, I506V, I507V on a portion of CFTR Exon 10. The DNA sequence is SEQ ID NO:5, and the amino acid sequence is SEQ ID NO:6.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual,* and *Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach,* 1984, IRL Press, London, Nelson and Cox (2000), Lehninger *Principles of Biochemistry* 3rd Ed., W. H. Freeman Pub., New York, N.Y. and Berg et al. (2002) *Biochemistry,* 5th Ed., W. H. Freeman Pub., New York, N.Y., all of which are herein incorporated in their entirety by reference for all purposes.

As used herein, "homozygous" refers a genotype consisting of two identical alleles at a given locus.

As used herein, "heterozygous" refers to a genotype consisting of two different alleles at a locus.

As used herein, "variant" refers to a permanent change in the DNA sequence of a gene, including mutations. Variants and mutations in a gene's DNA sequence can alter the amino acid sequence of the protein encoded by the gene.

As used herein, "benign variant" refers to an alteration in a gene distinct from the normal, wild-type allele that does not appear to have a deleterious physiological effect on the patient carrying the variant.

As used herein, "locus of interest" refers to a sequence of nucleotides on a nucleic acid/amplicon that is to be detected and/or analyzed. The locus of interest can be a site where variants/mutations are known to cause disease or predispose to a disease state. A locus of interest can be a site of targeted nucleic acid variant within the context of a gene.

As used herein, "target nucleic acid" refers to one or more DNA or RNA molecule(s) that is to be replicated, amplified, detected, and/or analyzed. A "target nucleic acid" refers to deoxyribonucleic acid, ribonucleic acid or mixtures thereof. In addition, a "target nucleic acid" can further comprise non-natural nucleic acids. The target nucleic acid can be generated by any number of means. For example, it can be generated from a cleavage reaction by a restriction enzyme or other endo- or exonucleases. Alternatively, it can form as a result of a specific or non-specific cleavage of a longer nucleic acid strand, and can be generated enzymatically or chemically. The target nucleic acid of the present invention also contemplates fragments generated naturally in vivo, by aged tissue, apoptotic cells, or the consequence of any other natural, biological or chemical reaction that may generate nucleic acid fragments. The target nucleic acid may contain the locus of interest as a portion of its sequence or the locus of interest may make up the entire sequence of the target nucleic acid.

As used herein, "probe-amplicon elements" and "probe/primer amplicon" refer to the nucleic acid fragments or amplicons that are generated during PCR using a primer and a probe.

As provided throughout the specification, the steps of all of the methods described herein can occur in a sequential or simultaneous manner, and alternatively some portion of the steps can occur simultaneously while others occur sequentially.

Some embodiments of the present invention utilize thermal melt curves to distinguish between at least two variants on a target nucleic acid having a locus of interest. Thermal melt curves of fluorescence have been used in the art to determine the melting temperature of a DNA strand when denatured from the duplex state to the two separate single strands via a ramp increase in temperature. Typically, the melting temperature or Tm is defined to be the temperature at which 50% of the paired DNA strands have denatured into single strands. Intercalating dyes that fluoresce when bound to double stranded DNA and lose their fluorescence when denatured are often used in measuring Tm. Typically, the negative derivative of fluorescence with respect to temperature (−dF/dT) has been used in the determination of Tm. In typical systems, the temperature at the peak −dF/dT is used as an estimate of the melting temperature Tm.

Melting curve analysis is typically carried out either in a stopped flow format or in a continuous flow format. In one example of a stopped flow format, melting curve analysis is done in a chamber to which the nucleic acid sample has been added. In an alternative stopped flow format, flow is stopped within a microchannel of a microfluidic device while the temperature in that channel is ramped through a range of temperatures required to generate the desired melt curve. In one example of a continuous flow format, a melting curve analysis is performed by applying a temperature gradient along the length (direction of flow) of a microchannel of a microfluidic device. If the melting curve analysis requires that the molecules being analyzed be subjected to a range of temperatures extending from a first temperature to a second temperature, the temperature at one end of the microchannel is controlled to the first temperature, and the temperature at the other end of the length is controlled to the second temperature, thus creating a continuous temperature gradient spanning the temperature range between the first and second selected temperatures. An example of an instrument for performing a melting curve analysis is disclosed in U.S. Patent Application Publication No. 2007/0231799, incorporated herein by reference in its entirety.

The thermal melt data that is analyzed in accordance with aspects of the present invention is obtained by techniques well known in the art. See, e.g., Knight et al. (U.S. Patent Application Publication No. 2007/0231799); Knapp et al. (U.S. Patent Application Publication No. 2002/0197630); Wittwer et al. (U.S. Patent Application Publication No. 2007/0020672); and Wittwer et al. (U.S. Pat. No. 6,174,670). Although the present invention is applicable to the analysis of thermal melt data obtained in any environment, it is particularly useful for thermal melt data obtained in the microfluidic environment because of the need for greater sensitivity in this environment.

Thermal melt data is typically generated by elevating the temperature of a molecule or molecules, e.g., of one or more nucleic acids, for a selected period of time and measuring a detectable property emanating from the molecule or molecules, wherein the detectable property indicates an extent of denaturation of the nucleic acid. This period of time can range, for example, from about 0.01 second through to about 1.0 minute or more, from about 0.01 second to about 10 seconds or more, or from about 0.1 second to about 1.0 second or more, including all time periods in between. In one embodiment, heating comprises elevating the temperature of the molecule or molecules by continuously increasing the temperature of the molecule or molecules. For example, the temperature of the molecule(s) can be continuously increased at a rate in the range of about 0.1° C./second to about 1° C./second. Alternatively, the temperature of the molecule(s) can be continuously increase at a slower rate, such as a rate in the range of about 0.01° C./second to about 0.1° C./second, or at a faster rate, such as a rate in the range of about 1° C./second to about 10° C./second. The heating can occur through application of an internal or an external heat source, as is known in the art.

The actual detection of a change(s) in a physical property of the molecules can be detected in numerous methods depending on the specific molecules and reactions involved. For example, the denaturation of the molecules can be tracked by following fluorescence or emitted light from molecules in the assay. The degree of, or change in, fluorescence is correlational or proportional to the degree of change in conformation of the molecules being assayed. Thus, in some methods, the detection of a property of the molecule(s) comprises detecting a level of fluorescence or emitted light from the molecules(s) that varies as a function of relative amounts of binding. In one configuration, the detecting of fluorescence involves a first molecule and a second molecule, wherein the first molecule is a fluorescence indicator dye or a fluorescence indicator molecule and the second molecule is the target molecule to be assayed. In one embodiment, the fluorescence indicator dye or fluorescence indicator molecule binds or associates with the second molecule by binding to hydrophobic or hydrophilic residues on the second molecule. The methods of detecting optionally further comprise exciting the fluorescence indicator dye or fluorescence indicator molecule to create an excited fluorescence indicator dye or excited fluorescence indicator molecule and discerning and measuring an emission or quenching event of the excited fluorescence indicator dye or fluorescence indicator molecule. See, e.g., Boles et al. (U.S. Patent Application Publication No. 2009/0112484); Cao et al. (U.S. Patent Application Publication No. 2009/0112481); Knight et al. (U.S. Patent Application Publication No. 2007/0231799), which are incorporated herein by reference.

Several techniques exist for the measurement of the denaturation of the molecules of interest, and any of these can be used in generating the data to be analyzed in accordance with aspects of the present invention. Such techniques include fluorescence, fluorescence polarization, fluorescence resonance energy transfer, circular dichroism and UV absorbance. Briefly, the fluorescence techniques involves the use of spectroscopy to measure changes in fluorescence or light to track the denaturation/unfolding of the target molecule as the target molecule is subjected to changes in temperature. Spectrometry, e.g. via fluorescence, is a useful method of detecting thermally induced denaturation/unfolding of molecules. Many different methods involving fluorescence are available for detecting denaturation of molecules (e.g. intrinsic fluorescence, numerous fluorescence indicator dyes or molecules, fluorescence polarization, fluorescence resonance energy transfer, etc.) and are optional embodiments of the present invention. These methods can take advantage of either internal fluorescent properties of target molecules or external fluorescence, i.e. the fluorescence of additional indicator molecules involved in the analysis. See, e.g., Cao (U.S. Patent Application Publication No. 2010/0233687), incorporated herein by reference in its entirety.

One method of measuring the degree of denaturation/unfolding of the target molecule is through monitoring of the fluorescence of dyes or molecules added to the microfluidic device along with the target molecule and any test molecules of interest. A fluorescence dye or molecule refers to any fluorescent molecule or compound (e.g., a fluorophore) which can bind to a target molecule either once the target molecule is unfolded or denatured or before the target molecule undergoes conformational change by, for example, denaturing and which emits fluorescent energy or light after it is excited by, for example, light of a specified wavelength.

One dye type typically used in the microfluidic devices is one that intercalates within strands of nucleic acids. An example of such a dye is ethidium bromide. An exemplary use of ethidium bromide for binding assays includes, for example, monitoring for a decrease in fluorescence emission from ethidium bromide due to binding of test molecules to nucleic acid target molecules (ethidium bromide displacement assay). See, e.g., Lee et al. (J Med Chem 36:863-870, 1993). The use of nucleic acid intercalating agents in measurement of denaturation is known to those in the art. See, e.g., Haugland (Handbook of Fluorescent Probes and Research Chemicals, 9$^{th}$ Ed., Molecular Probes, Inc., Eugene, Oreg., 2002).

Dyes that bind to nucleic acids by mechanisms other than intercalation are also typically employed in thermal melt analysis. For example, dyes that bind the minor groove of double stranded DNA can be used to monitor the molecular unfolding/denaturation of the target molecule due to temperature. Examples of suitable minor groove binding dyes are the SYBR® Green family of dyes sold by Molecular Probes Inc. (Eugene, Oreg., USA). See, e.g., Haugland (Handbook of Fluorescent Probes and Research Chemicals, 9$^{th}$ Ed., Molecular Probes, Inc., Eugene, Oreg., 2002). SYBR® Green dyes will bind to any double stranded DNA molecule. When a SYBR Green dye binds to double stranded DNA, the intensity of the fluorescent emissions increases. As more double stranded DNA are denatured due to increasing temperature, the SYBR® Green dye signal will decrease. Other suitable dyes are LCGreen® Plus sold by Idaho Technology, Inc. (Salt Lake City, Utah, USA), SYTO® 9 sold by Invitrogen Corp. (Carlsbad, Calif.) and, Eva Green® sold by Biotium Inc. (Hayward, Calif.). Further examples of dyes include SYBR® Green I (BIORAD, Hercules, Calif.), ethidium bromide, SYBR® Gold (INVITROGEN), Pico Green, TOTO-1 and YOYO-1. It is within the skill of persons of ordinary skill in the art to select a suitable dye.

In accordance with aspects of the present invention, methods, kits, primers, probes, and systems for distinguishing between nucleotide variants that are close in proximity on a gene are provided. In one exemplary embodiment, the method of the present invention is useful for distinguishing between nucleotide variants that are in close proximity of the CFTR gene, such as those found in Exon 10, in order to reliably detect and diagnose disease-causing CF genotypes. The present invention can also be suitably applied to distinguish between other nucleotide variants that are close in proximity, e.g., mutations of G551D and R553X of Exon 11 on the CFTR gene. G551D, a disease-causing mutation of a single base change from G to A (position of c.1652), has 4% frequency among CF patients, and is only 4 bp from R553X, another disease-causing mutation of a single base change from C to T. Both mutations have been genotyped with the dual primer (one of which is limited and one of which is in excess) and unlabeled probe design described herein. Similarly, the present invention can also be used to identify G551S, a mutation that can remarkably reduce single-channel open probability, and is another single base mutation from G to A on the position of c.1651. It is theorized that distinguishing G551D and R553X from G551S may require the use of an additional unlabelled probe. Thus, it is within the scope of the present invention that multiple assays, each using a limiting primer and an excess primer in combination with an unlabeled probe can be used to distinguish between two or more nucleotide variants. For instance, in some cases, distinguishing between three nucleotide variants may require three assays, each having its own limiting primer and an excess primer in combination with an unlabeled probe.

FIG. 1 illustrates a gene map of one embodiment of the invention showing the mutations of ΔF508, ΔI507, F508C, I506V, I507V on a portion of CFTR Exon 10. ΔI507, a three base pair in frame deletion close to ΔF508, results in the deletion of isoleucine. ΔF508 can occur due to deletion of either TCT or CTT. Both 3 base pair deletions of TCT or CTT lead to the same DNA sequence-ATTTG when ΔF508 mutation presents. ΔI507, on the other hand, presents a much less severe phenotype compared to ΔF508. There are two consecutive isoleucine codons (ATC) between nucleotides 1515 and 1522 having the sequence: A(1516)T(1517)C(1518)A(1519)T(1520)C(1521). Deletion of any 3 base pairs in the range of between 1516 and 1521 would produce the same sequence. The benign variants, F508C, I507V and I506V, are located within the same region on Exon 10 as ΔI507 and ΔF508. Identification of disease-causing variants ΔF508/ΔI507 is hindered by the presence of neighboring benign variants. The presence of variants in close proximity results in incorrect clinical diagnoses because the melting signatures for benign and disease-causing variants that are in close proximity are often not reliably discernible.

Figure 2:
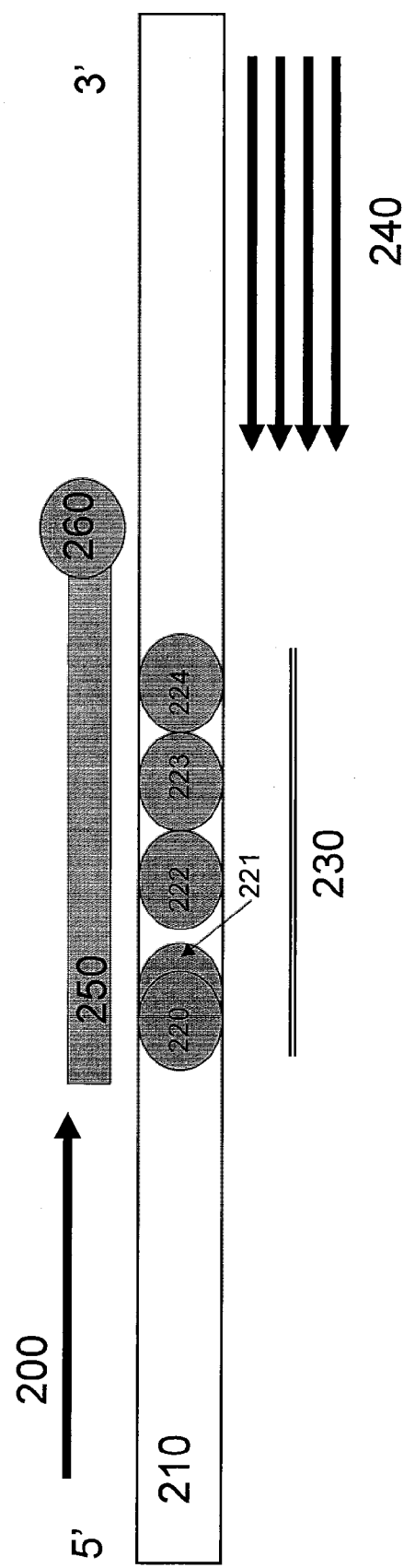
FIG. 2 illustrates a schematic diagram of the primers, probe, and target nucleic acid having a locus of interest.

FIG. 2 is a schematic diagram illustrating an embodiment of the present invention. A limiting primer (200) for amplification in the 5'-3' direction of a target double stranded nucleic acid (210) having mutations of interest (220-224) at a locus of interest (230) and an excess primer (240) for amplification of the target oligonucleotide (210) in the 3'-5' direction are used to produce small amplicons. An unlabeled probe (250) having a blocker (260) at its 3' end, and designed to hybridize to the reverse strand of the target nucleic acid (210) at the locus of interest (230), is used for high resolution thermal melting analysis. One or more additional unlabeled probes (not shown), which are also designed to hybridize to the reverse strand of the target nucleic acid (210) at the locus of interest (230), but having a sequence that is different from the first unlabeled probe (250), are used to obtain one or more additional high resolution thermal melting curves. The schematic mutations of interest (220-224) include benign variants (220, 222 and 224), as well as disease causing variants (221 and 223), all of which are located in close proximity to each other.

In accordance with a method of the present invention, an amplicon is provided which contains the locus of interest. The amplicon can be produced by any method that results in the amplification of a target nucleic acid. Amplification reactions are well known in the art, and the skilled artisan can readily use any suitable amplification reaction. PCR is perhaps the most well-known of a number of the different amplification techniques. In one embodiment, asymmetric PCR is utilized to generate the amplicon. As is well known in the art, asymmetric PCR uses one primer in a limiting concentration and the other primer in excess concentration to preferentially amplify one DNA strand in a double-stranded DNA template. It is typically used in sequencing and hybridization probing where amplification of only one of the two complementary strands is required. PCR is carried out as usual, but with an excess of the primer for the strand targeted for amplification. Because of the slow (arithmetic) amplification later in the reaction after the limiting primer has been used up, extra cycles of PCR are required. See Innis et al. (Proc Natl Acad Sci USA 85:9436-9440, 1988). A recent modification on this process, known as Linear-After-The-Exponential-PCR (LATE-PCR), uses a limiting primer with a higher Tm rather than the excess primer to maintain reaction efficiency as the limiting primer concentration decreases mid-reaction. See Pierce and Wangh (Methods Mol Med 132:65-85, 2007). In a preferred embodiment, basic asymmetric PCR is utilized to generate an amplicon having the locus of interest.

Thus, in one embodiment of a method in accordance with the present invention, asymmetric PCR is used to preferentially amplify one DNA strand of a target double stranded DNA template in order to produce amplicons having the locus of interest in order to distinguish between at least two variants on a target DNA. In a non-limiting embodiment, small amplicons having 45-130 base pairs, preferably 60-100 base pairs, are produced. Small amplicons usually have the advantages of efficient PCR, short cycles and distinguishable Tm separations for homozygote and a unique melting shape for heterozygotes. However, in many cases, the thermal melting of such small amplicons will not itself be able to differentiate nearby neighbor mutations/variants, e.g., CFTR ΔF508 and ΔI507 from F508C, I506V and I507V, due to the complexity of such close proximity variants/mutations. In accordance with the present invention, a plurality of unlabeled probes is utilized to distinguish the variants in the amplicon. As used herein, a plurality of probes refers to at least two probes. In one embodiment, the unlabeled probes have different lengths and/or different target specificities. Design considerations for the primers to produce the small amplicon and for the plurality of probes are described in further detail herein.

According to one aspect of the present invention, the method includes hybridizing different portions of a small amplicon produced by asymmetric PCR with different unlabeled probes. A single portion of the small amplicon hybridizes with a single unlabeled probe to produce a probe-amplicon element, such that a probe-amplicon element is produced for each of the plurality of unlabeled probes. For example, if two unlabeled probes are utilized, a first portion of the amplicon hybridizes with a first unlabeled probed to produce a first probe-amplicon element and a second portion of the amplicon hybridizes with a second unlabeled probed to produce a second probe-amplicon element. The probe-amplicon element can be formed in the presence of an indicator dye, such as any of those described herein and well known to the skilled artisan. The use of the unlabeled probes described herein produces unique melting signatures at lower temperature regions from the small amplicon Tm. Melting signature curves can be obtained by subjecting the dyed unlabeled probe-amplicon elements to high resolution thermal melting analysis as described herein. The method of the present invention, e.g., the use of a small amplicon and specially designed primers and probes, is capable of distinguishing variants that are in close proximity on a target nucleic acid.

In one embodiment, a biological sample containing a target nucleic acid having a locus of interest is subjected to asymmetric PCR to generate small amplicons having the locus of interest. The asymmetric PCR can be performed in any suitable instrument for performing PCR, including thermal cyclers and microfluidic devices well known to the skilled artisan. The reaction mixture containing the small amplicons having a locus of interest is divided into a plurality of portions to be kept separated. Each of the separate small amplicon portions is involved in hybridization with one of the plurality of unlabeled probes so that a plurality of amplicon-probe hybridization reactions occurs sequentially or simultaneously to produce a plurality of probe-amplicon elements. In one embodiment, each of the plurality of unlabeled probes is perfectly complementary to the wild-type sequence of the reverse strand of the target nucleic acid, but the individual unlabeled probes each have a different length.

In another embodiment of the invention, a biological sample containing a target nucleic acid having a locus of interest is divided into two or more portions. Each portion of the biological sample is then simultaneously or sequentially subjected to asymmetric PCR to generate small amplicons having the locus of interest, which are then subjected to hybridization with unlabeled probes so that a plurality of amplicon-probe hybridization reactions can be performed sequentially or simultaneously. In one embodiment, primers and an unlabeled probe are added to a divided portion of the biological sample for amplification, annealing and extension. Each of the individual divided sample portions is used for amplification in the presence of one of the unlabeled probes so that a plurality of amplification reactions is performed sequentially or simultaneously to produce a plurality of probe-amplicon elements. In one embodiment, each of the plurality of unlabeled probes is perfectly complementary to the wild-type sequence of the reverse strand of the target nucleic acid, but the individual unlabeled probes each have a different length.

In another aspect, a system for distinguishing between at least two nearby neighbor variants on a nucleic acid having a locus of interest according to the present invention is provided which may comprise (a) a microfluidic device comprising a plurality of sample loading zones, each of the sample loading zones being configured to house a separate asymmetric PCR using a nucleic acid having a locus of interest, wherein the microfluidic device comprises at least two sample loading zones that are loaded with a limiting primer, an excess primer, and an unlabeled probe, and wherein at least one of the at least two sample loading zones that are loaded with an unlabeled probe contains a first unlabeled probe as the loaded unlabeled probe and at least one of the at least two sample loading zones that are loaded with an unlabeled probe contains a second unlabeled probe as the loaded unlabeled probe; (b) a HRMA device, comprising a heating element, a fluorescence excitation light source and a fluorescence collection device, configured to thermally melt probe-amplicon elements obtained from asymmetric PCRs in the sample loading zones, and to generate fluorescence derivative melting curves for the probe-amplicon elements; and (c) a fluorescence derivative melting curve analysis device configured to compare at least two melting curves generated by the HRMA device so as to distinguish between at least two nearby neighbor variants on the nucleic acid having a locus of interest. Examples of microfluidic devices that can be used according to the system of the present invention are described in Hasson et al. (U.S. Patent Application Publication No. 2010/0191482), as well as others disclosed herein, which are incorporated herein by reference in their entirety. Examples of possible HRMA devices configured for fluorescence measurement are illustrated in U.S. Patent Application Publication Nos. 2008/0003593 and 2009/0324037 and U.S. Pat. No. 7,629,124, as well as others disclosed herein, which are incorporated herein by reference in their entirety. In one exemplary embodiment, a fluorescence derivative melting curve analysis device can be an appropriately programmed computer that can render and compare at least two melting curves generated by the HRMA device as disclosed herein. Conventional high resolution thermal melt software well known to the skilled artisan, including Genotype Determinator and Melt Viewer, can be used to recognize and compare the probe melting signatures of each genotype for targeted amplicons.

In one embodiment, amplification of the biological sample having a locus of interest and annealing and extension of the small amplicons produced by amplification are performed in a microfluidic device. In one embodiment, the microfluidic device has a plurality of channels for amplification, annealing and extension of one or more biological samples, or one or more portions of one biological sample, in parallel. In one embodiment, the microfluidic device has a plurality of wells for loading the biological sample onto the device. In another embodiment, the microfluidic device has a first part for performing PCR amplification and a second part for performing thermal melt analysis. A description of PCR amplification, and examples of microfluidic devices including thermal control elements for PCR amplification and thermal melt analysis are provided in U.S. Patent Application Publication Nos. 2009/0248349, 2009/0318306, 2009/0324037, 2010/0233687 and 2011/0056926, the entire disclosures of which are incorporated herein by reference.

Embodiments of the present invention can be used in a variety of instruments but are particularly useful in PCR and thermal melt systems that perform in vitro diagnostics. Embodiments of the present invention may be used in devices that are intended for thermal melt of samples (diagnostics) as well as other heaters and sensors within the instrument that perform entirely different functions (e.g., sample prep or PCR). Examples of microfluidic devices known in the art include, but are not limited to, Chow et al. (U.S. Pat. No. 6,447,661), Kopf-Sill (U.S. Pat. No. 6,524,830), Spaid (U.S. Pat. No. 7,101,467), Dubrow et al. (U.S. Pat. No. 7,303,727), Schembri (U.S. Pat. No. 7,390,457), Schembri (U.S. Pat. No. 7,402,279), Takahashi et al. (U.S. Pat. No. 7,604,938), Knapp et al. (U.S. Patent Application Publication No. 2005/0042639), and Hasson et al. (U.S. Patent Application Publication No. 2010/0191482), as well as others disclosed herein. Each of these patents or patent application publications is incorporated herein by reference.

In one or more embodiments of the invention, after amplification, annealing and extension, the probe-amplicon elements are subjected to saturation dyes and high resolution melting analysis in order to generate melting curves. Each probe-amplicon element can produce a unique signature melting curve because the length and/or target of the unlabeled probes used for hybridization in each run is different, thereby resulting in a different melt signature. When the targeted sequence contains disease-causing mutations/variants or nearby neighboring benign variant(s), during melting, the melting signatures of these mutations/variants can be definitively displayed on the probe melting region on the melting curve. Accordingly, analysis of the generated melting curves using two or more unlabeled probes for the target nucleic acid having a locus of interest makes it possible to discern between variants that are in close proximity on the target sequence. An example of one possible fluorescence measurement system is illustrated in U.S. Patent Application Publication Nos. 2008/0003593 and 2009/0324037 and U.S. Pat. No. 7,629,124, which are incorporated herein by reference in their entirety.

Figure 3:
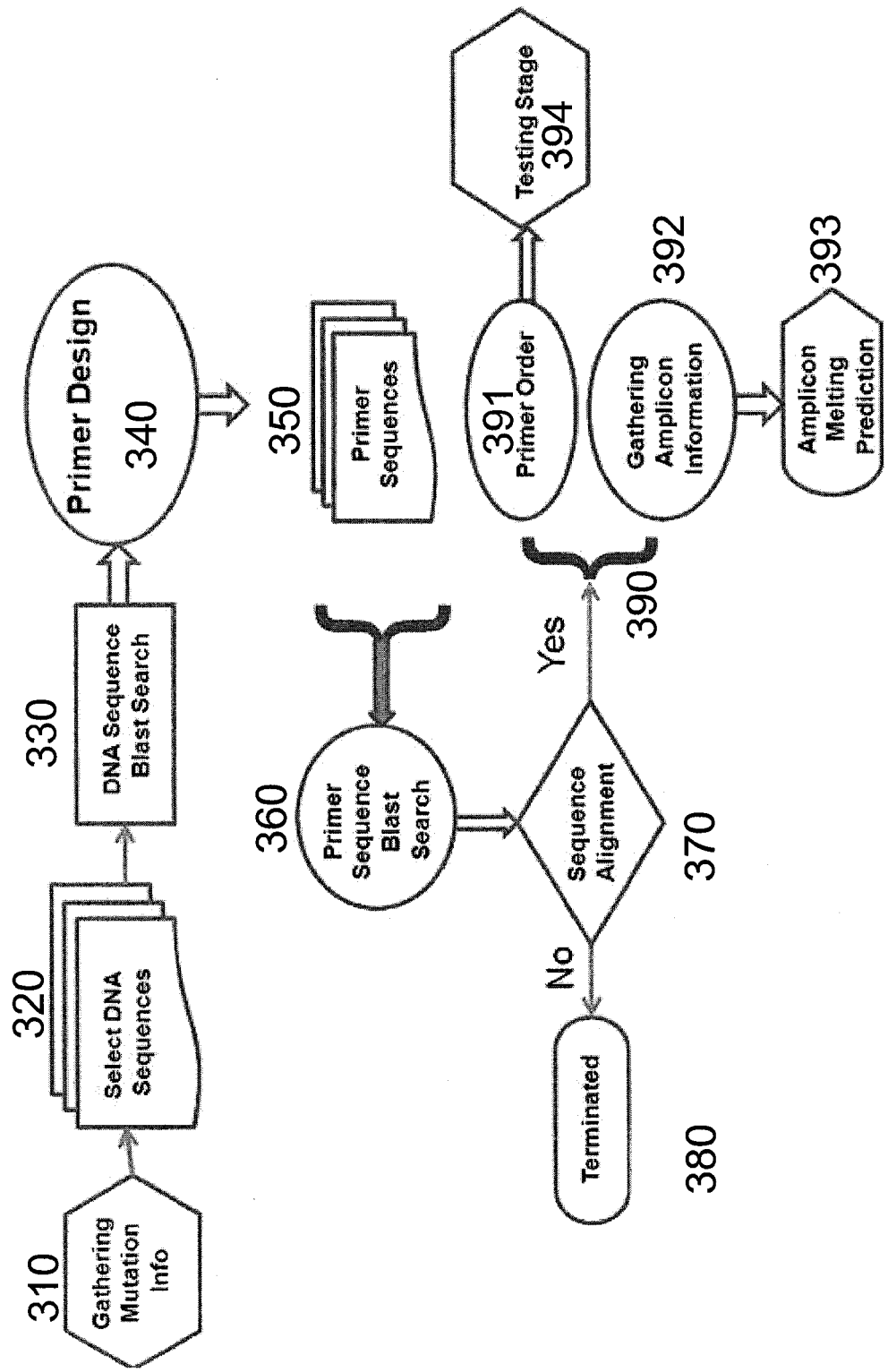
FIG. 3 is a flow-chart showing a primer design process in accordance with one embodiment of the present invention.

In order to distinguish among the variants that are close in proximity on the target nucleic acid, specially designed primers and unlabeled probes are used to produce the small amplicons and for the thermal melt analysis. FIG. 3 illustrates a flow chart for a method of designing primers according to one embodiment of the present invention. In one embodiment for designing primers, mutation information can be obtained (310), e.g., from the American College of Medical Genetics (ACMG) (www.acmg.net/Pages/ACMG_Activities/stds-2002/cf.htm). From this information, DNA sequences of interest for primer design can be selected (320). In an exemplary embodiment, the DNA sequences can be selected from the CFTR gene database (www.genet.sickkids.on.ca/PicturePage.html). In one embodiment, the DNA sequences are selected so that the mutation(s) of interest is located in about the middle of the sequence of interest, i.e., the sequence containing the mutation(s) of interest. The length of the selected DNA sequence can vary, but may be for example several hundred bps. In one embodiment, the DNA sequence may be about 150-500 bp in length. In an embodiment, the DNA sequence may be about 200-400 bp in length. In an embodiment, the DNA sequence may be 300 bp in length. Once selected, each DNA sequence of interest is compared with other sequences to define regions of local similarity between sequences for each of the DNA sequences of interest (330). In one embodiment, the other sequences can be found on NCBI sequence databases and blast search tools such as BLAST (blast.ncbi.nlm.nih.gov/Blast.cgi) and Human BLAST (genome.ucsc.edu/cgi-bin/hgBlat?command=start&org=Human&db=hg18&hgsid=151501082) can be used for comparisons. Primer design can then be implemented, e.g., by using primer design software. Examples of such software include, but are not limited to, Primer 3 software (frodo.wi.mit.edu/primer3/) or SNP Wizard software (courtesy of Carl Wittwer, University of Utah) (340) to produce primer sequences (350). Sequence similarity of primers output by the software and other sequences within the same genome are compared using tools such as BLAST and Human BLAST (360) to obtain sequence alignments (370). If the primer sequences are the same as other sequences within the same genome on multiple locations, e.g. on different chromosomes, or on the same chromosome, this primer is rejected (380). If the primer sequence is a unique sequence, which, in a preferred embodiment, is 100% different from any other sequences, this primer and/or probe are accepted (390). Once primer pairs are designed as described above and accepted (391), the primer pairs are checked with, for example, In-Silico PCR tool for PCR prediction for PCR conditions and products. An example of an In-Silico PCR tool includes, but is not limited to, (genome.ucsc.edu/cgi-bin/hgPcr?wp_target=&db=hg18&org=Human&wp_f=&wp_r=&wp_size=4000&wp_perfect=15&wp_good=15&wp_showPage=true&hgsid=151501082) (392). The accepted sequences can be examined for theoretical melting prediction (393). Examples of melt prediction software include, but are not limited to, UMelt software (courtesy of Carl Wittwer, University of Utah, www.dna.utah.edu/umelt/um.php) and Poland Melt Prediction software (www.biophys.uni-duesseldorf.de/local/POLAND/). In some embodiments, the wild type sequence and the mismatched sequence of the targeted mutations can be checked with both programs. The predicted results can be compared, recorded, and later used for comparing with experimental data as references. Once the primer sequences have passed the above criteria and checks, they can be tested for the assay feasibility, including sensitivity, specificity, and reproducibility of the assay (394).

In some embodiments, a primer pair is designed so that a forward primer is set as the limiting primer and a reverse primer is set as the excess primer in the asymmetric PCR. In other embodiments, a primer pair is designed so that a forward primer is set as the excess primer and a reverse primer is set as the limiting primer in the asymmetric PCR. Each primer is set close to the targeted variant region so that the amplicon size can be reduced for high genotyping sensitivity. In some embodiments, the primers are set from 20-80 nucleotides, preferably 25-70 nucleotides, more preferably 30-60 nucleotides from the targeted variant region. In some embodiments, the difference of the first primer's Tm and the second primer's Tm is less than about 1° C. In some embodiments, the Tm of each prime is, independently, between 52° C. and 65° C. In some embodiments, the primers are independently from about 15 to about 30 bp in length. In some embodiments, the primers are independently from 18 to 25 bp in length. In certain embodiments the primers are independently from 18-22 bp in length. In some embodiments, each primer has GC content between about 40-60%, independently. In certain embodiments, the primers are designed to avoid having more than three G or C nucleotides in the last 5 bases at the 3' end of the primers. In some embodiments, the primers are designed to have a maximum of four di-nucleotide repeats.

In certain embodiments, one or more unlabeled probes are designed that have a sequence that is complementary to the wild-type sequence. In one embodiment, the probes are designed under the same criteria as the primers for identical PCR conditions. After identifying the mutation and the locus of interest on a gene, probe design can be performed by placing the probe within the locus of interest region. The sequence can be aligned using the BLAST or HumanBlast tools previously mentioned. Using these tools, any probe sequences that are homologous to other regions of unrelated sequences should be excluded. In some embodiments, the probe is designed so as to have its Tm be less than about 70° C. In certain embodiments, the probe is designed so as to have its Tm be less than the Tm of the primers. In preferred embodiments, probes are designed so that the targeted nucleic acid variants are located at approximately the middle of the length of the probe.

In some embodiments, the unlabeled probes are perfectly complimentary to the wild-type sequence on the reverse strand of the target nucleic acid. In other embodiments, the unlabeled probes are perfectly complimentary to the wild-type sequence on the forward strand of the target nucleic acid. Thus, in individuals having mutations/variants at the locus of interest, the unlabeled probes will have one or more single base pair mismatch(es) at the corresponding locus. This design is to increase the assay sensitivity and specificity of all of the mutations/variants at the locus of interest on the target nucleic acid. Thus, in one embodiment, the length of the unlabeled probe is designed so as to have sufficient sensitivity and specificity to the mutations/variants within the locus of interest. In some embodiments, an unlabeled probe can be designed to have 2 to 5 nucleotides at its 5'-end prior to the locus of interest, preferably 2 or 3 nucleotides at its 5'-end prior to the targeted variants. In some embodiments, a second unlabeled probe has 5 to 8 nucleotides at its 5'-end prior to the targeted variants. In some embodiments, a first probe and a second probe are used for generating melting curves for the same biological sample, wherein the probes have different lengths. The length of the unlabeled probes can be varied depending on the melting characteristics of the targeted amplicons.

Generally, the longer the probe length, the stronger the probe melt signals. In an exemplary embodiment, when the probe length is about ⅓ of the amplicon size, the probe melt signals are significantly increased and easy to identify each targeted mutation. When the probe size is greater than ⅓ of amplicon size, the probe melt signal is remarkably strong and the fine separations between nearby mutations and signature melt shapes can be easily obtained. However, in some embodiments, the probe length can be less than ⅓ of the amplicon size.

In one embodiment, the probes are designed to have between 25-50 nucleotides, preferably between 30-40 nucleotides, more preferably between 33-39 nucleotides. The probe length is selected so to increase the probe melting signal strength. In certain exemplary embodiments, one unlabeled probe can be about 34 nucleotides in length while another unlabeled probe can be about 37 nucleotides in length. In some embodiments, a first probe and a second probe are each blocked at the 3' end to prevent extension of the probe. The 3' end may be blocked with any suitable blocker, for example, a 3' C6-amino blocker, a 3' phosphorylation blocker, or any other suitable 3' blockers. During probe design, the range of optimal Tms of probe is about 2-6° C. lower than primer Tms. In one embodiment, the probe Tm is less than about 5° C. lower than primer Tms. In another embodiment, the probe Tm is about 3° C. lower than primer Tms. Unlabeled probe design has been used to determine complex mutations on other genes. In some embodiments, the present invention can be used for Factor V Leiden genotyping, human platelet antigens, the RET proto-oncogene, lactase and hereditary hemorrhagic telangiectasia genotypings. In certain embodiments, care should be taken to avoid designing primers and probes that are the same at multiple locations.

One of the unique features of the present invention is the availability of multiple sources of data to distinguish between neighboring mutations. If two neighboring mutations cannot be clearly separated from the probe melt curves, then the amplicon melt curves should be used to identify these mutations. One of skill in the art will recognize that the assay procedure described herein results in the production of small double-stranded amplicons (from the primer/primer PCR) and single stranded probe/primer amplicons (from the unlabeled probe and excess primer PCR). Melting of the amplicons from the assay will provide thermal melt data for each type of amplicon, and therefore the data from both the small double-stranded amplicons and from the probe/primer amplicons can be used to distinguish between neighboring mutations. For instance, the low temperature region is the probe/primer melt region, which reflects fluorescence signal levels changes during the temperature transition when the probe was melted off from the amplicon. The higher temperature melt region presents the fluorescence signal changes during the double stranded amplicon melt. Usually, if the amplicon size is small, the changes in the double stranded amplicon melt curves can help to separate the variants that may be difficult to distinguish in the probe/primer melt region.

In view of the above design considerations, the present invention also provides a method of designing primers and probes that are useful for thermal melt analysis of a locus of interest that contains benign variants and disease-causing variants that are in close proximity. In accordance with this aspect, the method comprises selecting a locus of interest of a disease, in which the locus has benign variants and disease-causing variants in close proximity. In one embodiment, close proximity means within 3-15 nucleotides, preferably within 3-10 and more preferably within 3-7 nucleotides of each other. The method also comprises designing a pair of primers for use in asymmetric PCR. The primers have a Tm difference of less than about 1° C. and are selected to produce an amplicon of about 60 bp or longer. In some embodiments, the PCR produces amplicons that are between 70 and 130 bp in length. In certain embodiments, the PCR produces amplicons that are between 80 and 100 bp in length. The method further comprises designing at least two probes for hybridizing to one strand of the locus of interest. The nucleotide sequence of each probe is complementary to the wild-type sequence of the locus of interest. Each probe has a Tm that is less than 5° C. lower than the Tms of the primers. Each probe overlaps the nucleotide positions of the benign and disease-causing variants that are in close proximity. The probes can differ in length. In one embodiment, the probes differ in length on the 5' end of the probe. In another embodiment, the probes have a 3' end block to prevent extension. The probes and primers may further have the additional characteristics described herein.

According to one or more of the above embodiments, the present invention provides a method for detecting a disease in a patient based on the patient's genotype. In one embodiment, diagnosticians can take advantage of a priori knowledge of benign and disease-causing variant gene sequences associated with a target disease. In another embodiment, it is possible to use the present invention as a tool to identify and genotype benign variants and disease-causing variants associated with a particular disease based on analysis of the target sequence and melting signature curves obtained by using two or more unlabeled probes. In one embodiment, a first portion of a biological sample from a patient can be subjected to asymmetric PCR to produce a small amplicon having a locus of interest, which hybridizes to a first unlabeled probe to produce a first melting curve. A second portion of the biological sample can simultaneously or sequentially be subjected to asymmetric PCR to produce a small amplicon having a locus of interest, which hybridizes to a second unlabeled probe to produce a second melting curve. The unlabeled probes have different lengths and are selected in order to produce unique melting curves in each instance.

In another embodiment, a biological sample from a patient can be subjected to asymmetric PCR to produce a small amplicon having a locus of interest. A first portion of the small amplicon having a locus of interest is subjected to a first unlabeled probe assay to produce a first melting curve and a second portion of the small amplicon having a locus of interest is subjected to a second unlabeled probe assay to produce a second melting curve. A plurality of small amplicon portions can be subjected to unlabeled probe assays to obtain additional melting curves, in which unlabeled probes having different lengths are selected in order to produce unique melting curves in each instance.

The present invention provides a method to distinguish between a benign variant and a disease-causing neighbor variant by analyzing a first melting curve and a second melting curve, in which a probe melting signature curve of the benign variant and a probe melting signature curve of the disease-causing variant in the first and second melting curves are different. Accordingly, by reliably distinguishing between a benign variant and a disease-causing neighbor variant, the present invention makes it is possible to determine whether the patient has a disease-causing variant.

In another aspect, a biological sample from a patient can be divided into a first portion and at least a second portion. A plurality of additional portions may be used according to the steps described herein. In each portion, asymmetric PCR can be performed in order to produce a small amplicon having a locus of interest in each portion. The small amplicon having a locus of interest in each portion can be subjected to an unlabeled probe assay and high resolution thermal melt analysis in order to produce a unique melting curve for each portion. The unique signature melting curves can be analyzed in order to distinguish between a benign variant and a disease-causing neighbor variant. Accordingly, by reliably distinguishing between a benign variant and a disease-causing neighbor variant, it can be determined whether the patient has a disease-causing variant.

As described in one embodiment herein, an unlabeled probe assay includes the steps of hybridizing an unlabeled probe to a locus of interest on a small amplicon to form a probe-amplicon element, adding a saturated dye to the probe-amplicon element to form a mixture, and generating a melting curve for the probe-amplicon element by measuring fluorescence from the dye as the mixture is heated.

The above described embodiments of a multiple unlabeled probe assay in high resolution thermal melt analysis are simple, fast and can be easily adapted to microfluidic devices. The probe melting signatures of each genotype for targeted amplicons can be recognized using conventional high resolution thermal melt software well known to the skilled artisan, including Genotype Determinator and Melt Viewer. The definitive probe melting shapes of each genotype per each mutation generated with both probes can be used in a clinical molecular diagnostic report. The definitive probe melting shapes of each genotype per each mutation generated with both probes can be accepted and interpreted easily and clearly by clinicians and physicians. Probe/primer sets designed according to the present invention can be used to study various diseases, including, for example, Cystic Fibrosis. In one embodiment, the above described embodiments can be applied to a CFTR ACOG panel testing kit.

The panel recommended by The American College of Obstetricians and Gynecologists (ACOG) and the American College of Medical Genetics (ACMG) includes 23 core mutations on CF gene.

In another aspect, the present invention provides a kit for distinguishing between at least two variants on a target nucleic acid having a locus of interest and/or detecting a disease in a patient based on the patient's genotype. Unlabeled probes designed according to the present invention, along with primer pairs designed according to the present invention can be included in a kit for performing a diagnostic test for detecting a specified disease for which the probes and primers were designed. The kit may also be used for conducting biochemical studies on various nucleic acid sequences. The kit may include instructions for performing a diagnostic test. In a non-limiting example, a kit can contain primer pairs, two or more unlabeled probes, as well as instructions for performing a diagnostic test for detecting variants/mutations that are in close proximity using a target nucleic acid having a locus of interest. The kit can also contain common reagents necessary for PCR such as polymerases, ligases, NADP, dNTPs, buffers, salts, etc. Such reagents are known to persons of ordinary skill in the art.

Unlabeled probes and primer pairs designed according to the present invention can be used in any high resolution thermal melt analysis instrument for clinical molecular diagnosis on a target disease. Unlabeled probes and primer pairs designed according to the present invention can also be used by clinic laboratories for clinical molecular diagnosis of disease such as, for example, Cystic Fibrosis, Factor V Leiden genotyping, human platelet antigens, the RET proto-oncogene, lactase and hereditary hemorrhagic telangiectasia. Unlabeled probes and primer pairs designed according to the present invention can be used as a reflexive genotyping test following HRMA scanning of a gene by clinic laboratories for the clinical molecular diagnosis of a target disease.

The design concepts of the present invention can be applied both to similar close proximity variant/mutation situations on other genes of interest as well as to mutation discovery on other genes which have benign variants in close proximity to disease causing variants.

EXAMPLES

The present invention is described by reference to the following Examples, which are offered by way of illustration and are not intended to limit the invention in any manner. Standard techniques well known in the art or the techniques specifically described below were utilized.

Example 1

Figure 4:
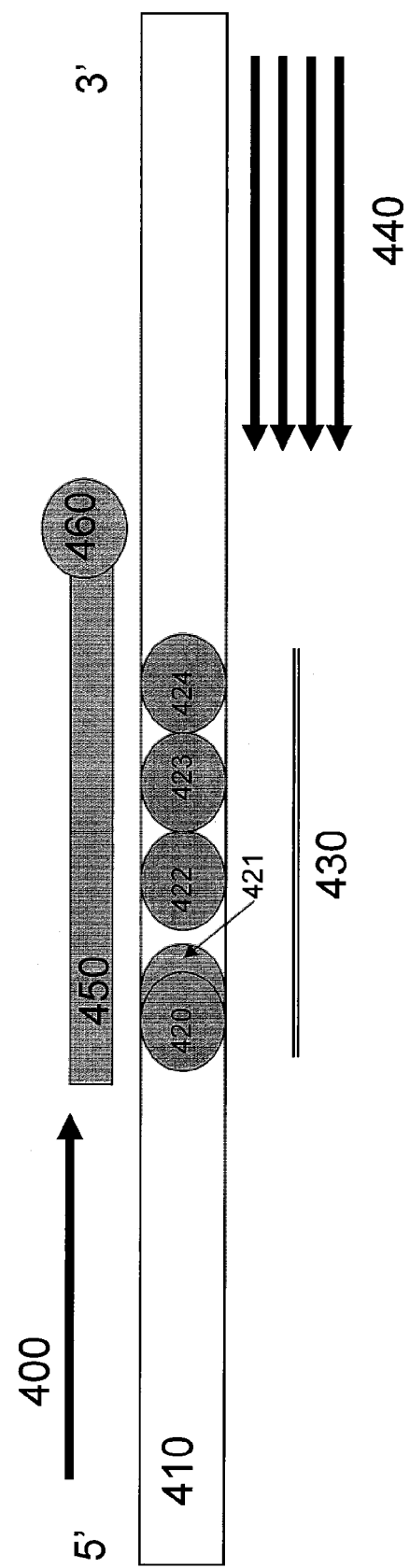
FIG. 4 illustrates a schematic diagram of the primers, probe, and a portion of CFTR Exon 10.

FIG. 4 illustrates a schematic diagram of primers, probes, and CFTR Exon 10. A forward primer (400), which acts as the limiting primer, extends in the 5' to 3' direction of the target nucleic acid having a locus of interest (410) having mutations of interest (420-424) at a locus of interest (430). The mutations of interest (420-424) include benign variants I506V (420), I507V (422), and F508C (424), as well as disease-causing variants ΔI507 (421) and ΔF508 (423). A reverse primer (440), which acts as the excess primer, extends in the 3' to 5' direction of the target nucleic acid having a locus of interest (410). Unlabeled probe (450) having a blocker (460) at its 3' end, has been designed to hybridize to the reverse strand of the target nucleic acid having a locus of interest (410) at the locus of interest (430).

In one non-limiting embodiment, a primer pair (F2/R4) that produces a specific amplicon that includes the mutations of ΔI507/ΔF508 and neighboring benign variants on Exon 10 can be used according to the present invention. F2 has the sequence 5'-GGATTATGCCTG GCACCATTA-3' (SEQ ID NO:1) and R4 has the sequence 5'-GTTGGCATGCTTT-GATG ACG-3' (SEQ ID NO:2).

In a non-limiting embodiment, two unlabeled probes (UP3 and UP4) that produce unique melting signature curves for the mutations of ΔI507/ΔF508 and neighboring benign variants on Exon 10 can be used according to the present invention. The sequence of the unlabeled probes was designed to be complementary to the wild type sequence of the region of interest on exon 10. UP3 has the sequence 5'-AAAATATCATCTTTGGTGTTTCCTATGATG AATATAG-3' (SEQ ID NO: 3) and UP4 has the sequence 5'-ATATCATCTTTGGTGTTTCCT ATGATGAATATAG-3' (SEQ ID NO:4). In individuals with ΔF508, ΔI507 or F508C, I506V, and I507V mutations, the probe will have a one or more base pair mismatch(es) at the corresponding locus. This design is to increase the assay sensitivity and specificity of all 5 mutations/variants in the mutation(s) of interest(s) on the DNA sequence of exon 10. UP3 possesses 5 bp prior to the mutation ΔI507 and I506V, and UP4 possesses 2 bp prior to the mutation ΔI507 and I506V.

Unlabeled probes designed according to the present invention, e.g., UP3 and UP4, along with primer pairs designed according to the present invention, e.g., F2 and R4, can be included in a kit for performing a diagnostic test for detecting a specified disease for which the probes and primers were designed. The kit may include instructions for performing a diagnostic test. In a non-limiting example, a kit can contain primer F2, primer R4, unlabeled probe UP3, and unlabeled probe UP4, as well as instructions for performing a diagnostic test for detecting cystic fibrosis transmembrane conductance regulator Exon 10 variants using a biological sample from a patient.

Example 2

Biological samples having a locus of interest (see details in Table 1) were incubated with limiting primer (F2), excess primer (R4), and an unlabeled probe (UP3). The two primers were provided in different concentrations along with buffer, dNTPs, MgCl2, LC Green Plus, and polymerase. Parallel mixtures using the same primers and reagents, but a different unlabeled probe (UP4), were also prepared. Each of the mixtures was loaded onto a 96-well plate on a LC 480 and subjected to asymmetric PCR. Initially, the PCRs preceded using the limiting and excess primers to produce small amplicons. In each mixture subjected to PCR, once the limiting primer was exhausted, the unlabeled probe then attached to the locus of interest on a small amplicon in conjunction with the excess primer and PCR continued. It is noted that the unlabeled probes each had a blocker in place so as to not extend during the PCRs.

TABLE 1

| NA01531 | Coriell | Exon 10 | deltaF508 | hom |
|---|---|---|---|---|
| NA07552 | Coriell | Exon 10/ Exon 11 | deltaF508/R553X | Compound het |
| NA11275 | Coriell | Exon 19/ Exon 10 | 3659delC/ deltaF508 | Compound het |
| NA11277 | Coriell | Exon 10 | delta I507 | het |
| NA11281 | Coriell | Intron 4/ Exon 10 | 621 + 1 G > T/F508 [PHE508DEL] | Compound het |
| NA11283 | Coriell | Exon 9/ Exon 10 | A455E/deltaF508 | Compound het |
| NA11284 | Coriell | Exon 11/ Exon 10 | R560T/deltaF508 | Compound het |

TABLE 1-continued

| NA13591 | Coriell | Exon 4/ Exon 10 | R117H/deltaF508 | Compound het |
|---|---|---|---|---|
| NA18799 | Coriell | Exon 13/ Exon 10 | 2184delA/ delta F508 | Compound het |
| NA18800 | Coriell | Intron 12/ Exon 10 | 1898 + 1G > A/ deltaF508 | Compound het |
| NA07469 | Coriell | Exon 11/ Exon 10 | 1789C > T/R553X/ deltaF508 | Compound het |
| NA07381 | Coriell | Intron 19/ Exon 10 | 3849 + 10kbC > T/ deltaF508 | Compound het |
| NA13033 | Corielle | Exon 10 | F508C | Hom |
| NA21551 | Corielle | Exon 10 | delta F508/I507V | Compound het |
| I506V | Utah | Exon 10 | 1648A/G | Het |

The PCR cycles were performed as detailed in Table 2:

TABLE 2

| | Unlabeled Probe Assay | | |
|---|---|---|---|
| PCR Cycling Setting | Cycle | Temperature ° C. | Duration (seconds) |
| Hot Start | 1 | 95 | 10 |
| PCR cycling | 60 | 94 | 5 |
| | | 58 | 5 |
| | | 72 | 6 |
| Pre-melt Denature & Re-nature | 1 | 94 | 5 |
| | | 45 | 3 |
| Melt | 1 | 95 | Ramp rate - 0.06° C./sec; 10 acquisition/° C. |
| | | 45 | 1 |

After completion of the PCR cycles, the probe-amplicon products in each portion were subjected to HRMA to produce unique melting signatures at lower temperature regions from the small amplicon Tm. The data showed that the primer pair (F2/R4) produced the specific amplicon that included the mutations of ΔI507/ΔF508 and neighboring benign variants on Exon 10. The data also showed that the unlabeled Probe UP3 placed mutation ΔI507 at the $6^{th}$ bp position.

Figure 5:
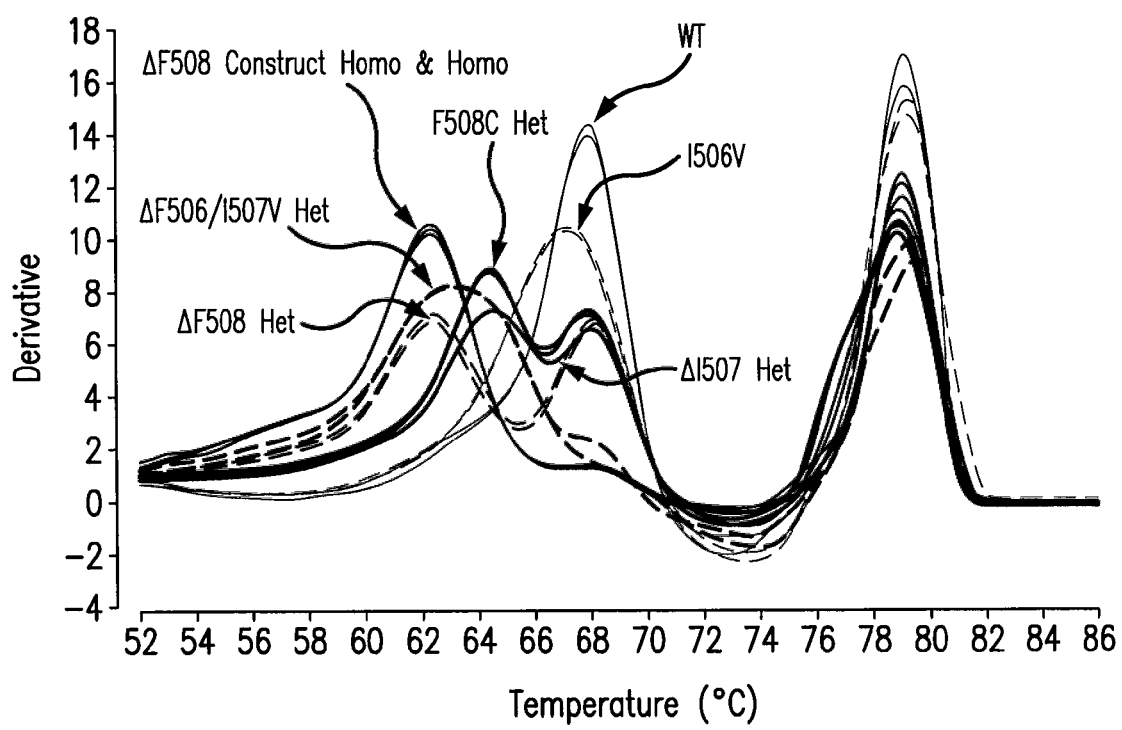
FIG. 5 is a high resolution melting curve profile for a portion of CFTR Exon 10 obtained using a first unlabeled probe.
Figure 6:
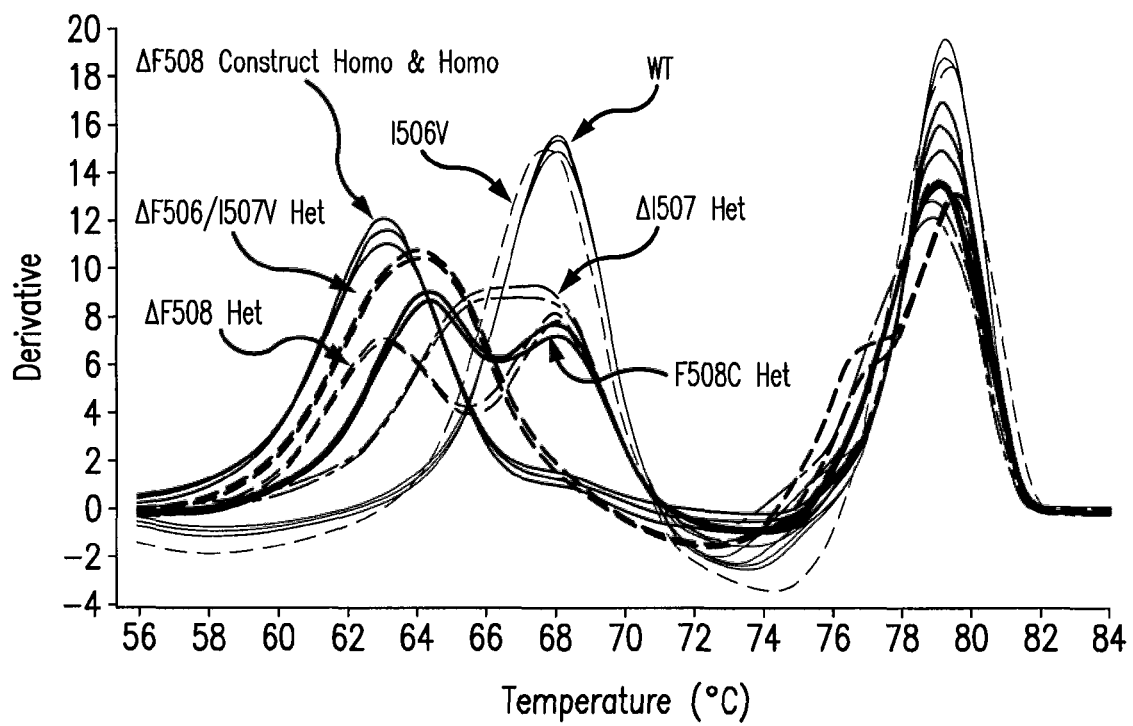
FIG. 6 is a high resolution melting curve profile for a portion of CFTR Exon 10 obtained using a second unlabeled probe.

Experiments using the unlabeled probes, primer pairs, and target nucleic acid having a locus of interest showed that all samples were amplified. This experiment was done several times using the Roche LightCycler® 480 (LC480) cycler platform and a microfluidic instrument. The results of the experiments are shown in FIGS. 5 and 6. FIGS. 5 and 6 illustrate a so-called "derivative plot" which describes the derivative of fluorescence with respect to temperature as a function of temperature (e.g., dF/dT vs. T). FIG. 5 illustrates thermal melt curves of an amplification product generated using the primer pairs and tested with the first unlabeled primer (UP3) on the microfluidic instrument. FIG. 6 illustrates thermal melt curves of an amplification product generated using the primer pairs and tested with the second unlabeled primer (UP4) on the microfluidic instrument.

FIG. 5 demonstrates that UP3 clearly distinguished the homozygous variant ΔF508, the compound heterozygote of ΔF508 and I507V, heterozygote of ΔF508, heterozygote of I506V and the wild-type. However, there is no significant difference between heterozygote of ΔI507 and F508C. Thus, the design of UP3 was found to present the melting signature of ΔI507 heterozygote with two melting peaks in the probe melting region, as well as definitively distinguish I506V benign variant from the wild-type and other mutations. However, the limitation for using this probe alone is that the difference between ΔI507 heterozygote and F508C heterozygote was not reliably distinguishable.

FIG. 6 demonstrates that UP4 clearly distinguished the homozygous of ΔF508, the compound heterozygote of ΔF508 and I507V, heterozygote of ΔF508, heterozygote of ΔI507, heterozygote of F508C and the wild-type. However, the I506V heterozygote was not reliably distinguishable from the wild-type.

Analysis of both melting signatures from the two tests were used to clearly identify and differentiate ΔF508 and ΔI507 and nearby neighboring benign variants, F508C, I506V, and I507V on exon 10.

Example 3

Primers and probes were designed for use in a Cystic Fibrosis American College of Obstetricians and Gynecologists (ACOG) panel. The ACOG panel included the primers and probes described in Examples 1 and 2, above. The sequences of these primers and probes are listed in Table 3 below and details pertaining thereto are listed in Table 4. Forward primers are denominated with the suffix "F#," reverse primers are denominated with the suffix "R#," and probes are denominated with the suffix "UP#."

TABLE 3

| Exon | Primer or Probe Name | Sequence 5'-3' | |
|---|---|---|---|
| 3 | Exon 3 G85E F1 | GCCCTTCGGCGATGTTTT | (SEQ ID NO: 7) |
|   | Exon 3 G85E R1 | gatccttacCCCTAAATATAAAAAG | (SEQ ID NO: 8) |
| 4 | Exon 4 R117H F3 | ATGACCCGGATAACAAGGAG | (SEQ ID NO: 9) |
|   | Exon 4 R117H R2 | CATAAGCCTATGCCTAGATAAATCG | (SEQ ID NO: 10) |
| Intron 4 | Exon 4 621 + 1G > T F2 | GAGAATAGCTATGTTTAGTTTGATTT | (SEQ ID NO: 11) |
|   | Exon 4 621 + 1G > T R3 | gcctgtgcaaggaagtatta | (SEQ ID NO: 12) |
| Intron 5 | Exon 5 711 + 1G > T F2 | GTCTCCTTTCCAACAACCTGAA | (SEQ ID NO: 13) |
|   | Exon 5 711 + 1G > T R1 | agtgcctaaaagattaaatcaa | (SEQ ID NO: 14) |
| 7 | Exon 7 R334W F2 | GCACTAATCAAAGGAATCATCCTC | (SEQ ID NO: 15) |
|   | Exon 7 R334W R2 | CAGAATGAGATGGTGGTGAAT | (SEQ ID NO: 16) |
| 7 | Exon 7 R347P F3 | CCACCATCTCATTCTGCATTG | (SEQ ID NO: 17) |
|   | Exon 7 R347P R2 | GGAAATTGCCGAGTGACC | (SEQ ID NO: 18) |
| 9 | Exon 9 A455E F1 | gggccatgtgcttttcaaact | (SEQ ID NO: 19) |
|   | Exon 9 A455E R1 | gaactacCTTGCCTGCTCCA | (SEQ ID NO: 20) |
|   | e9 A455E UP1r | AACCGCCAACAACTGTCCTCTTTCTAT | (SEQ ID NO: 21) |
| Intron 10 | Exon 11 1717 − 1 G > A F4 | AGTGACTCTCTAATTTTCTATTTTGGTAAT | (SEQ ID NO: 22) |
|   | Exon 11 1717 − 1 G > A R5 | CTCTGCAAACTTGGAGATGTC | (SEQ ID NO: 23) |
| e10 | Exon 10 507n508 F2 | GGATTATGCCTGGCACCATTA | (SEQ ID NO: 24) |
|   | Exon 10 507n508 R4 | GTTGGCATGCTTTGATGACG | (SEQ ID NO: 25) |
|   | e10 507n508 UP3 | AAAATATCATCTTTGGTGTTTCCTATGATGAATATAG | (SEQ ID NO: 26) |
|   | e10 507n508 UP4 | ATATCATCTTTGGTGTTTCCTATGATGAATATAG | (SEQ ID NO: 27) |
| 11 | Exon 11 G542X F8 | GTTTGCAGAGAAAGACAATATAGTTCT | (SEQ ID NO: 28) |
|   | Exon 11 G542X R7 | CTCAGTGTGATTCCACCTTCT | (SEQ ID NO: 29) |
| 11 | e11 551n553 F2 | GAGAAGGTGGAATCACACTG | (SEQ ID NO: 30) |
|   | e11 551n553 R4 | cagcaaatgcttgctagacc | (SEQ ID NO: 31) |
|   | e11 551n553 UP | GAGGTCAACGAGCAAGAATTTCTTTA | (SEQ ID NO: 32) |
| 11 | Exon 11 R560T F6 | AACGAGCAAGAATTTCTTTAGCA | (SEQ ID NO: 33) |
|   | Exon 11 R560T R3 | GCTTGCTAGACCAATAATTAGTTATTCAC | (SEQ ID NO: 34) |
| Intron 12 | Exon 12 1898 + 1G > A F2 | CCTAGATGTTTTAACAGAAAAGAAA | (SEQ ID NO: 35) |
|   | Exon 12 1898 + 1G > A R3 | gcattataagtaaggtattcaaagaac | (SEQ ID NO: 36) |
| 13 | Exon 13 2184delA F11 | GTCTCCTGGACAGAAACAAAAA | (SEQ ID NO: 37) |
|   | Exon 13 2184delA R10 | CCCAAACTCTCCAGTCTGTTTA | (SEQ ID NO: 38) |
| 14b | Exon 14 2789 + 5G > A F3 | GCTGTGGCTCCTTGGAAAgt | (SEQ ID NO: 30) |
|   | Exon 14 2789 + 5G > A R1 | cacaatctacacaataggacatgga | (SEQ ID NO: 40) |
| Intron 16 | Exon 16 3120 + 1G > A F3 | CTCTTACCATATTTGACTTCATCCA | (SEQ ID NO: 41) |
|   | Exon 16 3120 + 1G > A R1 | catacttaacggtacttattttacat | (SEQ ID NO: 42) |
| Intron 19 | Intron 19 3849 + 10kbC > T F3 | aagagtcttccatctgttgcagt | (SEQ ID NO: 43) |
|   | Intron 19 3849 + 10kbC > T R3 | gaacatttcctttcagggtgtc | (SEQ ID NO: 44) |
| 19 | Exon 19 R1162X C > T F1 | ttcagATGCGATCTGTGAGC | (SEQ ID NO: 45) |
|   | Exon 19 R1162X C > T R2 | CTGTTGGCATGTCAATGAACTT | (SEQ ID NO: 46) |
| 19 | Exon 19 3659delC F2 | ATTGACATGCCAACAGAAGG | (SEQ ID NO: 47) |
|   | Exon 19 3659delC R1 | CTTGTATGGTTTGGTTGACTTG | (SEQ ID NO: 48) |
| 20 | Exon 20 W1282X G > A F2 | GTCTTGGGATTCAATAACTTTGC | (SEQ ID NO: 49) |
|   | Exon 20 W1282X G > A R1 | ATCACTCCAAAGGCTTTCCT | (SEQ ID NO: 50) |

TABLE 3-continued

| Exon | Primer or Probe Name | Sequence 5'-3' | |
|---|---|---|---|
| 21 | Exon 21 N1303K C > G F3 | GAAAGTATTTATTTTTCTGGAACATTTAGAAAA | (SEQ ID NO: 51) |
|  | Exon 21 N1303K C > G R5 | CCACTGTTCATAGGGATCCAA | (SEQ ID NO: 52) |

TABLE 4

| Exon | Primer or Probe Name | Length (bp) | Ta/Cycle | Tm (° C.) | Amplicon Length | GC % |
|---|---|---|---|---|---|---|
| 3 | Exon 3 G85E F1 | 18 | 58/40 | 63 | 69 | 56 |
|  | Exon 3 G85E R1 | 25 |  | 55 |  | 32 |
| 4 | Exon 4 R117H F3 | 20 | 58/40 | 59 | 58 | 50 |
|  | Exon 4 R117H R2 | 25 |  | 60 |  | 40 |
| Intron 4 | Exon 4 621 + 1G > T F2 | 26 | 58/40 | 54 | 55 | 27 |
|  | Exon 4 621 + 1G > T R3 | 20 |  | 56 |  | 45 |
| Intron 5 | Exon 5 711 + 1G > T F2 | 22 | 58/40 | 61 | 68 | 45 |
|  | Exon 5 711 + 1 G > T R1 | 22 |  | 53 |  | 27 |
| 7 | Exon 7 R334W F2 | 24 | 58/40 | 60 | 53 | 42 |
|  | Exon 7 R334W R2 | 21 |  | 57 |  | 43 |
| 7 | Exon 7 R347P F3 | 21 | 58/40 | 61 | 52 | 48 |
|  | Exon 7 R347P R2 | 18 |  | 59 |  | 56 |
| 9 | Exon 9 A455E F1 | 21 | 58/60 | 63 | 304 | 48 |
|  | Exon 9 A455E R1 | 20 |  | 60 |  | 55 |
|  | e9 A455E UP1r | 27 |  | 56 |  | 32 |
| Intron 10 | Exon 11 1717-1 G > A F4 | 31 | 58/40 | 61 | 54 | 26 |
|  | Exon 11 1717-1 G > A R5 | 21 |  | 60 |  | 48 |
| 10 | Exon 10 507n508 F2 | 21 | 58/60 | 62 | 90 | 48 |
|  | Exon 10 507n508 R4 | 20 |  | 63 |  | 50 |
|  | e10 507n508 UP3 | 37 |  | 58 |  | 29 |
|  | e10 507n508 UP4 | 34 |  | 57 |  | 29 |
| 11 | Exon 11 G542X F8 | 27 | 58/40 | 61 | 51 | 33 |
|  | Exon 11 G542X R7 | 21 |  | 61 |  | 48 |
|  | e11 551n553 F2 | 20 | 58/60 | 55 | 92 | 50 |
|  | e11 551n553 R4 | 20 |  | 59 |  | 50 |
|  | e11 551n553 UP | 26 |  | 55 |  | 38 |
| 11 | Exon 11 R560T F6 | 23 | 58/40 | 60 | 54 | 35 |
|  | Exon 11 R560T R3 | 29 |  | 62 |  | 34 |
| Intron 12 | Exon 12 1898 + 1G > A F2 | 26 | 58/40 | 57 | 67 | 27 |
|  | Exon 12 1898 + 1G > A R3 | 27 |  | 56 |  | 30 |
| 13 | Exon 13 2184delA F11 | 22 | 58/40 | 58 | 54 | 41 |
|  | Exon 13 2184delA R10 | 22 |  | 58 |  | 45 |
| 14b | Exon 14 2789 + 5G > A F3 | 20 | 58/40 | 62 | 51 | 55 |
|  | Exon 14 2789 + 5G > A R1 | 25 |  | 60 |  | 40 |
| Intron 16 | Exon 16 3120 + 1G > A F3 | 25 | 58/40 | 59 | 55 | 36 |
|  | Exon 16 3120 + 1G > A R1 | 27 |  | 54 |  | 26 |
| Intron 19 | Intron 19 3849 + 10kbC > T F3 | 23 | 58/40 | 59 | 62 | 43 |
|  | Intron 19 3849 + 10kbC > T R3 | 22 |  | 60 |  | 45 |
| 19 | Exon 19 R1162X C > T F1 | 20 | 58/40 | 60 | 51 | 50 |
|  | Exon 19 R1162X C > T R2 | 22 |  | 60 |  | 41 |
| 19 | Exon 19 3659delC F2 | 20 | 58/40 | 59 | 51 | 45 |
|  | Exon 19 3659delC R1 | 22 |  | 57 |  | 41 |
| 20 | Exon 20 W1282X G > A F2 | 23 | 58/40 | 59 | 51 | 39 |
|  | Exon 20 W1282X G > A R1 | 20 |  | 58 |  | 45 |
| 21 | Exon 21 N1303K C > G F3 | 34 | 58/40 | 60 | 58 | 21 |
|  | Exon 21 N1303K C > G R5 | 21 |  | 61 |  | 48 |

As shown by the above examples, two or more unlabeled probes may be used to provide a reliable procedure to discern between benign variants and disease-causing variants that are close in proximity on a gene.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. In addition, recitation of ranges of values herein are merely intended to serve as a shorthand method of referring to all separate ranges falling within the range, unless otherwise indicated, and each separate range is incorporated into the specification as if it were individually recited herein. For example, if the range 10-15 is disclosed, then the ranges 10-14, 10-13, 10-12, 10-11, 11-15, 11-14, 11-13, 11-12, 12-15, 12-14, 12-13, 13-15, 13-14 and 14-15 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of distinguishing between at least two nearby neighbor variants on a locus of interest on a gene, the method comprising:
 (a) providing a first aliquot of said nucleic acid having the locus of interest;
 (b) incubating said first aliquot of said nucleic acid with a limiting primer, an excess primer, and a first probe that is designed to hybridize to said locus of interest on a target strand of said nucleic acid;
 (c) performing asymmetric PCR using said first aliquot to produce an excess of amplicons corresponding to the target strand to which the first probe hybridizes, thereby producing a first probe element;
 (d) providing a second aliquot of said nucleic acid target having the locus of interest;
 (e) incubating said second aliquot of said nucleic acid target with said limiting primer, said excess primer, and a second probe that is designed to hybridize to said locus of interest on the target strand, wherein said first probe differs in sequence from said second probe in length;
 (f) performing asymmetric PCR using said second aliquot to produce an excess of amplicons corresponding to the target strand to which the second probe hybridizes, thereby producing a second probe element, wherein said first probe and said second probe each have a sequence that is complementary to a wild-type sequence of the target strand, each of said first and second probes covering the same at least two nearby neighbor variants;
 (g) generating a first melting curve for the first probe element in a first mixture with a saturating binding dye by measuring fluorescence from said dye as the first mixture is heated;
 (h) generating a second melting curve for the second probe element in a second mixture with said saturating binding dye by measuring fluorescence from said dye as the second mixture is heated; and
 (i) analyzing said first melting curve and said second melting curve to distinguish between said at least two nearby neighbor variants, wherein a melting signature curve of each of said at least two nearby neighbor variants is different in said first and second melting curves.

2. The method of claim 1, wherein said one or both of said first and second probes are unlabeled.

3. The method of claim 1, wherein steps (a)-(f) are performed simultaneously.

4. The method of claim 1, wherein steps (a)-(f) are performed sequentially.

5. The method of claim 1, wherein the limiting primer and the excess primer are each set close to the variants to reduce the amplicon size for high genotyping sensitivity.

6. The method of claim 1, wherein each of said first and second probes has one or more base pair mismatches at the locus of interest.

7. The method of claim 6, wherein each of said first and second probes has 2 to 5 base pair mismatches at the locus of interest.

8. The method of claim 1, wherein each of said first and second probes, independently, has 2 to 5 base pairs at its 5'-end prior to the locus of interest.

9. The method of claim 1, wherein the first probe has 2 or 3 base pairs at its 5'-end prior to the locus of interest.

10. The method of claim 1, wherein the second probe has 5 base pairs at its 5'-end prior to the mutation.

11. The method of claim 1, wherein the Tm of each of the first and second probes is less than about 5 degrees lower than the Tms of the limiting and excess primers and the difference of the limiting primer's Tm and the excess primer's Tm is less than about 1° C.

12. The method of claim 1, wherein said first probe and said second probe are 34 to 37 bp in length.

13. The method of claim 1, wherein said first probe and said second probe are blocked at their 3' ends.

14. The method of claim 1, wherein said locus of interest is on a gene associated with a disorder selected from the group consisting of Cystic Fibrosis, Factor V Leiden, human platelet antigens, a RET proto-oncogene associated disease, lactase hemorrhagic telangiectasia, and hereditary hemorrhagic telangiectasia.

15. The method of claim 1, wherein said locus of interest is Exon 11 of Cystic Fibrosis transmembrane conductance regulator gene.

16. The method of claim 1, wherein said locus of interest is Exon 10 of Cystic Fibrosis transmembrane conductance regulator gene.

17. The method of claim 16, wherein said limiting primer has a nucleotide sequence of 5'-GGATTATGCCTGGCAC-CATTA-3' (SEQ ID NO: 1).

18. The method of claim 16, wherein said excess primer has a nucleotide sequence of 5'-GT TGGCATGCTTTGAT-GACG-3' (SEQ ID NO: 2).

19. The method of claim 16, wherein said first probe is an unlabeled probe having a nucleotide sequence of 5'-AAAATATCATCTTTGGTGTTTCCTATGAT-GAATATAG-3' (SEQ ID NO:3).

20. The method of claim 19, wherein said first unlabeled probe is blocked at its 3' end.

21. The method of claim 16, wherein said second probe is an unlabeled probe having a nucleotide sequence of 5'-ATATCATCTTTGGTGTTTCCTATGATGAATATAG-3' (SEQ ID NO: 4).

22. The method of claim 21, wherein said second unlabeled probe is blocked at its 3' end.

23. The method of claim 16, wherein said at least two nearby neighbor variants are ΔI507 and F508C.

24. A method of distinguishing between at least two nearby neighbor variants on a locus of interest on a gene, the method comprising:
 (a) mixing a first portion of a target nucleic acid having the locus of interest with a first primer and a second primer, the primers configured for amplifying the target nucleic acid having the locus of interest, and a first unlabeled probe;

(b) in parallel, mixing a second portion of said target nucleic acid having the locus of interest with said first primer, said second primer, and a second unlabeled probe, wherein said first unlabeled probe and said second unlabeled probe each have a sequence that is complementary to a wild-type sequence of the target nucleic acid, each of said first and second probes covering the same at least two nearby neighbor variants;

(c) simultaneously amplifying the target nucleic acid having a locus of interest to generate amplicons having the locus of interest that hybridizes to said first unlabeled probe and to said second unlabeled probe to form a first probe element and a second probe element, respectively, wherein said first unlabeled probe differs in sequence from said second unlabeled probe in length;

(d) generating a first melting curve for the first probe element in the presence of a saturating binding dye by measuring fluorescence from said dye as the mixture is heated;

(e) generating a second melting curve for the second probe element in the presence of said saturating binding dye by measuring fluorescence from said dye as the mixture is heated; and (f) analyzing said first melting curve and said second melting curve to distinguish between said at least two nearby neighbor variants, wherein a probe melting signature curve of each of said at least two nearby neighbor variants is different in said first and second melting curves.

25. A method of detecting a disease in a patient based on said patient's genotype and a priori knowledge of nearby neighbor benign and disease-causing variants on a gene associated with said disease, comprising:

(a) obtaining a biological sample from said patient;

(b) subjecting a first portion of said biological sample to asymmetric PCR involving a limiting primer, an excess primer, and a first probe to produce a first probe-amplicon element;

(c) subjecting a second portion of said biological sample to asymmetric PCR involving said limiting primer, said excess primer, and a second probe to produce a second probe-amplicon element, each of the first and second probes covering both the benign variant and the disease-causing variant;

(d) generating a first melting curve and a second melting curve by subjecting said first and second probe-amplicon melting elements to high resolution thermal melting analysis, respectively, wherein said first probe and said second probe each have a sequence that is complementary to a wild-type sequence of the gene;

(e) distinguishing between the benign variant and the disease-causing neighbor variant by analyzing said first melting curve and said second melting curve, wherein a probe melting signature curve of said benign variant and a probe melting signature curve of said disease-causing variant in said first and second melting curves are different; and (f) determining whether said patient has a disease-causing variant.

26. The method of claim 25, wherein said disease is selected from the group consisting of Cystic Fibrosis, Factor V Leiden, human platelet antigens, a RET proto-oncogene associated disease, lactase hemorrhagic telangiectasia, and hereditary hemorrhagic telangiectasia.

27. The method of claim 26, wherein said disease cystic fibrosis.

28. The method of claim 25, wherein said benign and said disease-causing variant are neighboring variants.

29. The method of claim 28, wherein said benign variant is F508C and said disease-causing variant is ΔI507.

30. The method of claim 25, wherein said limiting primer has a nucleotide sequence of 5'-GGATTATGCCTGGCAC-CATTA-3' (SEQ ID NO: 1).

31. The method of claim 25, wherein said excess primer has a nucleotide sequence of 5'-GTTGGCATGCTTTGAT-GACG-3' (SEQ ID NO: 2).

32. The method of claim 25, wherein said first probe has a nucleotide sequence of 5'-AAAATATCATCTTTGGT-GTTTCCTATGATGAATATAG-3' (SEQ ID NO: 3).

33. The method of claim 32, wherein said first probe is blocked at its 3' end.

34. The method of claim 25, wherein said second probe has a nucleotide sequence of 5'-ATATCATCTTTGGT-GTTTCCTATGATGAATATAG-3' (SEQ ID NO: 4).

35. The method of claim 34, wherein said second probe is blocked at its 3' end.

36. A method of detecting a disease in a patient based on said patient's genotype and a priori knowledge of nearby neighbor benign and disease-causing variants associated with said disease, comprising:

(a) obtaining a biological sample from said patient;

(b) dividing said biological sample into a first portion and a second portion;

(c) performing asymmetric PCR in order to produce a small amplicon including both the benign variant and the disease-causing variant in each of said first portion and said second portion;

(d) subjecting said first portion to a first unlabeled probe assay to produce a first melting curve;

(e) subjecting said second portion to a second unlabeled probe assay to produce a second melting curve, each of the first and second probes covering both the benign variant and the disease-causing variant, wherein said first unlabeled probe and said second unlabeled probe each have a sequence that is complementary to a wild-type sequence of the gene;

(f) distinguishing between the benign variant and the disease-causing neighbor variant by comparing said first melting curve and said second melting curve, wherein a probe melting signature curve of said benign variant and a probe melting signature curve of said disease-causing variant in said first and second melting curves are different; and (g) determining whether said patient has a disease-causing variant.

37. The method of claim 36, wherein said first unlabeled probe assay comprises hybridizing a first unlabeled probe to a locus of interest on said small amplicon to form a first probe element, adding a saturated dye to said first probe element to form a mixture, and generating a first melting curve for the first probe element by measuring fluorescence from said dye as the mixture is heated.

38. The method of claim 36, wherein said second unlabeled probe assay comprises hybridizing a second unlabeled probe to a locus of interest on said small amplicon to form a second probe element, adding a saturated dye to said second probe element to form a mixture, and generating a second melting curve for the second probe element by measuring fluorescence from said dye as the mixture is heated.

39. The method of claim 36, wherein said disease is selected from the group consisting of Cystic Fibrosis, Factor V Leiden, human platelet antigens, a RET proto-oncogene associated disease, lactase hemorrhagic telangiectasia, and hereditary hemorrhagic telangiectasia.

40. A method of distinguishing between at least two nearby neighbor variants on a locus of interest on a gene, the method comprising:
   (a) providing an amplicon having the locus of interest;
   (b) hybridizing a first unlabeled probe to said locus of interest on a first portion of the amplicon to form a first probe element;
   (c) hybridizing a second unlabeled probe to said locus of interest on a second portion of the amplicon to form a second probe element, wherein said first unlabeled probe differs in sequence from said second unlabeled probe, wherein said first unlabeled probe and said second unlabeled probe each have a sequence that is complementary to a wild-type sequence of the gene, each of said first and second probes covering the same at least two nearby neighbor variants;
   (d) generating a first melting curve for the first probe element in a first mixture with a saturating binding dye by measuring fluorescence from said dye as the first mixture is heated;
   (e) generating a second melting curve for the second probe element in a second mixture said saturating binding dye by measuring fluorescence from said dye as the second mixture is heated; and
   (f) analyzing said first melting curve and said second melting curve to distinguish between said at least two nearby neighbor variants, wherein a melting signature curve of each of said at least two nearby neighbor variants is different in said first and second melting curves.

41. The method of claim 40, wherein said amplicon is produced by mixing a target nucleic acid having a locus of interest with a first primer and a second primer, the primers configured for amplifying the target nucleic acid having a locus of interest, and amplifying the target nucleic acid having a locus of interest to generate an amplicon.

42. The method of claim 40, wherein said amplicon is produced using asymmetric PCR.

43. The method of claim 40, wherein steps (a)-(f) are performed simultaneously.

44. The method of claim 40, wherein steps (a)-(f) are performed sequentially.

45. The method of claim 40, wherein the first primer and the second primer are each set close to the variants to reduce the amplicon size for high genotyping sensitivity.

46. The method of claim 40, wherein the probe has one or more base pair mismatches at the locus of interest.

47. The method of claim 40, wherein each of the first and second unlabeled probes has 2 to 5 base pairs at its 5'-end prior to the locus of interest.

48. The method of claim 40, wherein the first unlabeled probe has 2 or 3 base pairs at its 5'-end prior to the locus of interest.

49. The method of claim 40, wherein the second unlabeled probe has 5 base pairs at its 5'-end prior to the mutation.

50. The method of claim 40, wherein the probe Tm is less than about 5 degrees lower than primer Tms and the difference of the first primer's Tm and the second primer's Tm is less than about 1° C.

51. The method of claim 40, wherein said first probe and said second probe are 34 to 37 bp in length.

52. The method of claim 40, wherein said first probe and said second probe are blocked at their 3' ends.

53. The method of claim 41, wherein the first primer is a limiting primer in an asymmetric PCR.

54. The method of claim 41, wherein the second primer is an excess primer in an asymmetric PCR.

55. The method of claim 40, wherein said locus of interest is Exon 10 of Cystic Fibrosis transmembrane conductance regulator gene.

56. The method of claim 40, wherein said locus of interest is Exon 11 of Cystic Fibrosis transmembrane conductance regulator gene.

57. A method of detecting a disease in a patient based on said patient's genotype and a priori knowledge of nearby benign and disease-causing variants on a gene associated with said disease, comprising:
   (a) obtaining a biological sample from said patient;
   (b) subjecting said sample to asymmetric PCR to produce a small amplicon containing the benign variant and the disease-causing variant;
   (c) subjecting a first portion of said small amplicon to a first unlabeled probe assay to produce a first melting curve;
   (d) subjecting a second portion of said small amplicon to a second unlabeled probe assay to produce a second melting curve, each of the first and second probes covering both the benign variant and the disease-causing variant, wherein said first unlabeled probe and said second unlabeled probe each have a sequence that is complementary to a wild-type sequence of the gene;
   (e) distinguishing between the benign variant and the disease-causing neighbor variant by analyzing said first melting curve and said second melting curve, wherein a probe melting signature curve of said benign variant and a probe melting signature curve of said disease-causing variant in said first and second melting curves are different; and
   (f) determining whether said patient has a disease-causing variant.

* * * * *

SEQUENCE LISTING

```
<160> NUMBER OF SEQ ID NOS: 52

<210> SEQ ID NO 1
<211> LENGTH: 21
<212> TYPE: DNA
<213> ORGANISM: Homo sapiens

<400> SEQUENCE: 1
ggattatgcc tggcaccatt a                                        21

<210> SEQ ID NO 2
<211> LENGTH: 20
<212> TYPE: DNA
<213> ORGANISM: Homo sapiens

<400> SEQUENCE: 2
gttggcatgc tttgatgacg                                          20

<210> SEQ ID NO 3
<211> LENGTH: 37
<212> TYPE: DNA
<213> ORGANISM: Homo sapiens

<400> SEQUENCE: 3
aaaatatcat ctttggtgtt tcctatgatg aatatag                       37

<210> SEQ ID NO 4
<211> LENGTH: 34
<212> TYPE: DNA
<213> ORGANISM: Homo sapiens

<400> SEQUENCE: 4
atatcatctt tggtgtttcc tatgatgaat atag                          34

<210> SEQ ID NO 5
<211> LENGTH: 192
<212> TYPE: DNA
<213> ORGANISM: Homo sapiens
<220> FEATURE:
<221> NAME/KEY: CDS
<222> LOCATION: (1)..(192)

<400> SEQUENCE: 5 act tca ctt cta atg atg att atg gga gaa ctg gag cct tca gag ggt     48
Thr Ser Leu Leu Met Met Ile Met Gly Glu Leu Glu Pro Ser Glu Gly
1               5                   10                  15 aaa att aag cac agt gga aga att tca ttc tgt tct cag ttt tcc tgg     96
Lys Ile Lys His Ser Gly Arg Ile Ser Phe Cys Ser Gln Phe Ser Trp
            20                  25                  30 att atg cct ggc acc att aaa gaa aat atc atc ttt ggt gtt tcc tat    144
Ile Met Pro Gly Thr Ile Lys Glu Asn Ile Ile Phe Gly Val Ser Tyr
        35                  40                  45 gat gaa tat aga tac aga agc gtc atc aaa gca tgc caa cta gaa gag    192
Asp Glu Tyr Arg Tyr Arg Ser Val Ile Lys Ala Cys Gln Leu Glu Glu
```

<210> SEQ ID NO 6
<211> LENGTH: 64
<212> TYPE: PRT
<213> ORGANISM: Homo sapiens

<400> SEQUENCE: 6

Thr Ser Leu Leu Met Met Ile Met Gly Glu Leu Glu Pro Ser Glu Gly
1               5                   10                  15

Lys Ile Lys His Ser Gly Arg Ile Ser Phe Cys Ser Gln Phe Ser Trp
            20                  25                  30

Ile Met Pro Gly Thr Ile Lys Glu Asn Ile Ile Phe Gly Val Ser Tyr
        35                  40                  45

Asp Glu Tyr Arg Tyr Arg Ser Val Ile Lys Ala Cys Gln Leu Glu Glu
    50                  55                  60

<210> SEQ ID NO 7
<211> LENGTH: 18
<212> TYPE: DNA
<213> ORGANISM: Homo sapiens

<400> SEQUENCE: 7
gcccttcggc gatgtttt                                           18

<210> SEQ ID NO 8
<211> LENGTH: 25
<212> TYPE: DNA
<213> ORGANISM: Homo sapiens

<400> SEQUENCE: 8
gatccttacc cctaaatata aaaag                                   25

<210> SEQ ID NO 9
<211> LENGTH: 20
<212> TYPE: DNA
<213> ORGANISM: Homo sapiens

<400> SEQUENCE: 9
atgacccgga taacaaggag                                         20

<210> SEQ ID NO 10
<211> LENGTH: 25
<212> TYPE: DNA
<213> ORGANISM: Homo sapiens

<400> SEQUENCE: 10
cataagccta tgcctagata aatcg                                   25

<210> SEQ ID NO 11
<211> LENGTH: 26
<212> TYPE: DNA
<213> ORGANISM: Homo sapiens

<400> SEQUENCE: 11
gagaatagct atgtttagtt tgattt                                  26

<210> SEQ ID NO 12
<211> LENGTH: 20
<212> TYPE: DNA
<213> ORGANISM: Homo sapiens

<400> SEQUENCE: 12

-continued

```
gcctgtgcaa ggaagtatta                                               20

<210> SEQ ID NO 13
<211> LENGTH: 22
<212> TYPE: DNA
<213> ORGANISM: Homo sapiens

<400> SEQUENCE: 13
gtctcctttc caacaacctg aa                                            22

<210> SEQ ID NO 14
<211> LENGTH: 22
<212> TYPE: DNA
<213> ORGANISM: Homo sapiens

<400> SEQUENCE: 14
agtgcctaaa agattaaatc aa                                            22

<210> SEQ ID NO 15
<211> LENGTH: 24
<212> TYPE: DNA
<213> ORGANISM: Homo sapiens

<400> SEQUENCE: 15
gcactaatca aaggaatcat cctc                                          24

<210> SEQ ID NO 16
<211> LENGTH: 21
<212> TYPE: DNA
<213> ORGANISM: Homo sapiens

<400> SEQUENCE: 16
cagaatgaga tggtggtgaa t                                             21

<210> SEQ ID NO 17
<211> LENGTH: 21
<212> TYPE: DNA
<213> ORGANISM: Homo sapiens

<400> SEQUENCE: 17
ccaccatctc attctgcatt g                                             21

<210> SEQ ID NO 18
<211> LENGTH: 18
<212> TYPE: DNA
<213> ORGANISM: Homo sapiens

<400> SEQUENCE: 18
ggaaattgcc gagtgacc                                                 18

<210> SEQ ID NO 19
<211> LENGTH: 21
<212> TYPE: DNA
<213> ORGANISM: Homo sapiens

<400> SEQUENCE: 19
gggccatgtg cttttcaaac t                                             21

<210> SEQ ID NO 20
<211> LENGTH: 20
<212> TYPE: DNA
<213> ORGANISM: Homo sapiens
```

```
<400> SEQUENCE: 20
gaactacctt gcctgctcca                                            20

<210> SEQ ID NO 21
<211> LENGTH: 27
<212> TYPE: DNA
<213> ORGANISM: Homo sapiens

<400> SEQUENCE: 21
aaccgccaac aactgtcctc tttctat                                    27

<210> SEQ ID NO 22
<211> LENGTH: 31
<212> TYPE: DNA
<213> ORGANISM: Homo sapiens

<400> SEQUENCE: 22
agtgactctc taattttcta ttttggtaa t                                31

<210> SEQ ID NO 23
<211> LENGTH: 21
<212> TYPE: DNA
<213> ORGANISM: Homo sapiens

<400> SEQUENCE: 23
ctctgcaaac ttggagatgt c                                          21

<210> SEQ ID NO 24
<211> LENGTH: 21
<212> TYPE: DNA
<213> ORGANISM: Homo sapiens

<400> SEQUENCE: 24
ggattatgcc tggcaccatt a                                          21

<210> SEQ ID NO 25
<211> LENGTH: 20
<212> TYPE: DNA
<213> ORGANISM: Homo sapiens

<400> SEQUENCE: 25
gttggcatgc tttgatgacg                                            20

<210> SEQ ID NO 26
<211> LENGTH: 37
<212> TYPE: DNA
<213> ORGANISM: Homo sapiens

<400> SEQUENCE: 26
aaaatatcat ctttggtgtt tcctatgatg aatatag                         37

<210> SEQ ID NO 27
<211> LENGTH: 34
<212> TYPE: DNA
<213> ORGANISM: Homo sapiens

<400> SEQUENCE: 27
atatcatctt tggtgtttcc tatgatgaat atag                            34

<210> SEQ ID NO 28
<211> LENGTH: 27
<212> TYPE: DNA
<213> ORGANISM: Homo sapiens
```

```
<400> SEQUENCE: 28
gtttgcagag aaagacaata tagttct                                    27

<210> SEQ ID NO 29
<211> LENGTH: 21
<212> TYPE: DNA
<213> ORGANISM: Homo sapiens

<400> SEQUENCE: 29
ctcagtgtga ttccaccttc t                                          21

<210> SEQ ID NO 30
<211> LENGTH: 20
<212> TYPE: DNA
<213> ORGANISM: Homo sapiens

<400> SEQUENCE: 30
gagaaggtgg aatcacactg                                            20

<210> SEQ ID NO 31
<211> LENGTH: 20
<212> TYPE: DNA
<213> ORGANISM: Homo sapiens

<400> SEQUENCE: 31
cagcaaatgc ttgctagacc                                            20

<210> SEQ ID NO 32
<211> LENGTH: 26
<212> TYPE: DNA
<213> ORGANISM: Homo sapiens

<400> SEQUENCE: 32
gaggtcaacg agcaagaatt tcttta                                     26

<210> SEQ ID NO 33
<211> LENGTH: 23
<212> TYPE: DNA
<213> ORGANISM: Homo sapiens

<400> SEQUENCE: 33
aacgagcaag aatttcttta gca                                        23

<210> SEQ ID NO 34
<211> LENGTH: 29
<212> TYPE: DNA
<213> ORGANISM: Homo sapiens

<400> SEQUENCE: 34
gcttgctaga ccaataatta gttattcac                                  29

<210> SEQ ID NO 35
<211> LENGTH: 26
<212> TYPE: DNA
<213> ORGANISM: Homo sapiens

<400> SEQUENCE: 35
cctagatgtt ttaacagaaa aagaaa                                     26

<210> SEQ ID NO 36
<211> LENGTH: 27
<212> TYPE: DNA
```

<213> ORGANISM: Homo sapiens

<400> SEQUENCE: 36
gcattataag taaggtattc aaagaac                                27

<210> SEQ ID NO 37
<211> LENGTH: 22
<212> TYPE: DNA
<213> ORGANISM: Homo sapiens

<400> SEQUENCE: 37
gtctcctgga cagaaacaaa aa                                    22

<210> SEQ ID NO 38
<211> LENGTH: 22
<212> TYPE: DNA
<213> ORGANISM: Homo sapiens

<400> SEQUENCE: 38
cccaaactct ccagtctgtt ta                                    22

<210> SEQ ID NO 39
<211> LENGTH: 20
<212> TYPE: DNA
<213> ORGANISM: Homo sapiens

<400> SEQUENCE: 39
gctgtggctc cttggaaagt                                       20

<210> SEQ ID NO 40
<211> LENGTH: 25
<212> TYPE: DNA
<213> ORGANISM: Homo sapiens

<400> SEQUENCE: 40
cacaatctac acaataggac atgga                                 25

<210> SEQ ID NO 41
<211> LENGTH: 25
<212> TYPE: DNA
<213> ORGANISM: Homo sapiens

<400> SEQUENCE: 41
ctcttaccat atttgacttc atcca                                 25

<210> SEQ ID NO 42
<211> LENGTH: 27
<212> TYPE: DNA
<213> ORGANISM: Homo sapiens

<400> SEQUENCE: 42
catacttaac ggtacttatt tttacat                               27

<210> SEQ ID NO 43
<211> LENGTH: 23
<212> TYPE: DNA
<213> ORGANISM: Homo sapiens

<400> SEQUENCE: 43
aagagtcttc catctgttgc agt                                   23

<210> SEQ ID NO 44
<211> LENGTH: 22

```
<212> TYPE: DNA
<213> ORGANISM: Homo sapiens

<400> SEQUENCE: 44
gaacatttcc tttcagggtg tc                                      22

<210> SEQ ID NO 45
<211> LENGTH: 20
<212> TYPE: DNA
<213> ORGANISM: Homo sapiens

<400> SEQUENCE: 45
ttcagatgcg atctgtgagc                                         20

<210> SEQ ID NO 46
<211> LENGTH: 22
<212> TYPE: DNA
<213> ORGANISM: Homo sapiens

<400> SEQUENCE: 46
ctgttggcat gtcaatgaac tt                                      22

<210> SEQ ID NO 47
<211> LENGTH: 20
<212> TYPE: DNA
<213> ORGANISM: Homo sapiens

<400> SEQUENCE: 47
attgacatgc caacagaagg                                         20

<210> SEQ ID NO 48
<211> LENGTH: 22
<212> TYPE: DNA
<213> ORGANISM: Homo sapiens

<400> SEQUENCE: 48
cttgtatggt ttggttgact tg                                      22

<210> SEQ ID NO 49
<211> LENGTH: 23
<212> TYPE: DNA
<213> ORGANISM: Homo sapiens

<400> SEQUENCE: 49
gtcttgggat tcaataactt tgc                                     23

<210> SEQ ID NO 50
<211> LENGTH: 20
<212> TYPE: DNA
<213> ORGANISM: Homo sapiens

<400> SEQUENCE: 50
atcactccaa aggctttcct                                         20

<210> SEQ ID NO 51
<211> LENGTH: 34
<212> TYPE: DNA
<213> ORGANISM: Homo sapiens

<400> SEQUENCE: 51
gaaagtattt atttttctg gaacatttag aaaa                          34

<210> SEQ ID NO 52
```

```
<211> LENGTH: 21
<212> TYPE: DNA
<213> ORGANISM: Homo sapiens

<400> SEQUENCE: 52
ccactgttca tagggatcca a                                              21
```